United States Patent [19]

Katsube et al.

[11] Patent Number: 5,296,122
[45] Date of Patent: Mar. 22, 1994

[54] APPARATUS FOR FORMING THIN FILM

[75] Inventors: Teruaki Katsube, Tokyo; Shuichiro Yamaguchi; Naoto Uchida, both of Kanagawa; Takeshi Shimomura, Kanagawa, all of Japan

[73] Assignees: Teruaki Katsube, Tama; Terumo Kabushiki Kaisha, Shibuya, both of Japan

[21] Appl. No.: 837,873

[22] Filed: Feb. 18, 1992

Related U.S. Application Data

[62] Division of Ser. No. 500,293, Mar. 28, 1990, abandoned.

[30] Foreign Application Priority Data

| | | | |
|---|---|---|---|
| Mar. 29, 1989 | [JP] | Japan | 1-77814 |
| Jun. 19, 1989 | [JP] | Japan | 1-156603 |
| Aug. 9, 1989 | [JP] | Japan | 1-206136 |
| Aug. 25, 1989 | [JP] | Japan | 1-219040 |

[51] Int. Cl.$^5$ ............................................. C23C 14/46
[52] U.S. Cl. ................................ 204/298.04; 204/192.11
[58] Field of Search ........................... 204/192.11, 298.04

[56] References Cited

U.S. PATENT DOCUMENTS

| | | | |
|---|---|---|---|
| 4,142,958 | 3/1979 | Wei et al. | 204/192.11 |
| 4,278,890 | 7/1981 | Gruen et al. | 250/492.3 |
| 4,419,203 | 12/1983 | Harper et al. | 204/192.11 |
| 4,877,504 | 10/1989 | Lee | 204/192.11 |
| 4,911,809 | 3/1990 | Wort et al. | 204/192.11 |
| 4,933,065 | 6/1990 | Seiler | 204/298.06 |

FOREIGN PATENT DOCUMENTS

| | | | |
|---|---|---|---|
| 3625700 | 2/1988 | Fed. Rep. of Germany | 204/298.04 |
| 62-214172 | 9/1987 | Japan | 204/298.04 |
| 63-53265 | 3/1988 | Japan | 204/298.04 |
| 1295465 | 11/1972 | United Kingdom | 204/298.04 |

OTHER PUBLICATIONS

M. Rost et al., *Thin Solid Films*, vol. 20, pp. S15–S19 (1974).

*Primary Examiner*—Aaron Weisstuch
*Attorney, Agent, or Firm*—Burns, Doane, Swecker & Mathis

[57] ABSTRACT

In the manufacture of a substrate with a hydrophobic film used for a reference electrode of an ion sensor or the like, a hydrophobic film is formed on a substrate by irradiating a target consisting of a hydrophobic compound with a neutral atom beam and thereby effecting sputtering. The apparatus for effecting the sputtering comprises a target base disposed in a vacuum chamber, an atom beam gun for irradiating a target on the target base with a neutral beam, a substrate base and a shutter for controlling the passage of sputtered particles. A thin film that is manufactured is suitable for an ion sensor, such as an ISFET or the like or an enzyme sensor.

8 Claims, 17 Drawing Sheets

APPARATUS FOR FORMING THIN FILM

This application is a application Ser. No. 07/500,293, filed Mar. 28, 1990, now abandoned.

BACKGROUND OF THE INVENTION

1. Field of the Invention

This invention relates to a method of forming on a substrate a thin film such as a functional film used as a reference electrode of an ion sensor, and apparatus for forming a thin film suitable for carrying out the method and a biosensor and chemical sensor such as an ISFET (ion sensitive field effect transistor) sensor having a thin film formed by the apparatus.

2. Description of the Prior Art

Ion sensors or the like generally use reference electrodes for reference potential generation. In the manufacture of this reference electrode, there have been many attempts of manufacturing hydrophobic organic thin films consisting of hydrophobic fluororesins, particularly polytetrafluoroethylene (available under a trademark "Teflon") by a dry process such as a deposition process or a sputtering process.

However, in a method of forming a thin film of a reference electrode by the prior art sputtering process or the like, it is very difficult to control film composition, directivity of film and polymerization degrees, and it has been impossible to form an organic thin film as designed on a substrate. In the sputtering process, heat is stored in a target by an accelerated beam, thus causing thermal damage to the target. This technical field is only in an initial stage, and it can be said that the selection of the kind of organic thin film and corresponding dry process determines the quality of the film and characteristics of the intended functional film.

As the above apparatus for manufacturing a thin film, used in the field of manufacture of semiconductors, there are known various CVD (chemical vapor deposition) apparatus for instance, thermal CVD, reduced pressure CVD, light CVD and plasma CVD apparatuses, sputtering apparatus and ICB (ion cluster beam) apparatus. In many of these apparatuses, film is formed in vacuum and under a somewhat high temperature condition.

Recently, there have been extensive studies with an aim of making use of organic thin films for improving the function of electronic devices. It is thought that organic thin films can find extensive applications for passivation films and sealing materials because it is possible to obtain films which have good machining properties and are chemically stable.

However, with such prior art apparatuses for dry state manufacturing of thin films it is necessary to form films at high temperatures. Therefore, it is very difficult to form organic substances capable of ready decomposition, particularly thin films of polymers. Further, it is difficult to form multi-layer bodies, laminations and mixtures of thin films.

By using the RF sputtering process or ion beam process it is possible to form multi-layer bodies and mixtures of thin films. These methods, however, lead to great damage with organic substances due to ion bombardment, and there is a high probability of fragmentation of molecules. Besides, there is a trend of introduction of ions. Further, it is impossible to form an insulating film.

As methods of forming thin film in a wet state, there are a LB (Langmuir Blodgett) process and an electrolytic process. In these processes, thin films can be formed at room temperature. However, substances which can be used for film formation are limited, and thus it is impossible to obtain a perfect insulating film.

Further, regarding a sensor using a substrate with a thin film as electrode, ion sensors utilizing MOSFETs capable of fine machining using semiconductor manufacture technology, i.e., ISFET sensors, have been developed as solid-state very small sensors, with reported sizes less than 10 microns.

While the active electrode of the sensor is capable of miniaturization in this way, miniaturization of the whole sensor requires miniaturization of the reference electrodes.

With the prior art technique, however, it is difficult to obtain miniaturized solid reference electrodes. In order to solve these problems, reference electrodes with polystyrene thin film and hydrophobic organic polymer film on a gate insulating film are disclosed in Japanese Patent Disclosures 58-103658 and 58-34352.

While various reference electrodes have been developed for miniaturization and solidification, these electrodes can readily respond to pH (hydrogen ion concentration). In addition, adsorption of and permeation to interfering substances are possible. Therefore, these reference electrodes have inferior potential stability, and difficulties are involved in their use.

As further sensors, there are enzyme sensors for measuring the substrate concentration using enzyme electrodes by an amperometric process, and particularly enzyme sensors for directly measuring enzymic reaction from oxidation/reduction reaction of electron movement media (mediators).

These kinds of enzyme sensors are mainly used for clinical chemical analysis, and those for glucose, urea and neutral and phosphoric fat as the subject of measurement are in practical use. For instance, an enzymic reaction in the case of β-D-glucose (grape sugar) as the subject of measurement is expressed as

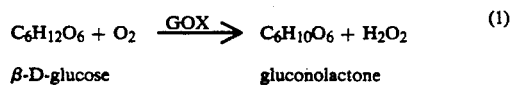

$$C_6H_{12}O_6 + O_2 \xrightarrow{GOX} C_6H_{10}O_6 + H_2O_2 \tag{1}$$

β-D-glucose    gluconolactone

More specifically, B-D-glucose consumes $O_2$ with an action of β-D-glucose (GOX) to generate an organic acid (gluconolactone) and hydrogen peroxide ($H_2O_2$). Therefore, glucose concentration can be measured from the amount of generated hydrogen peroxide and gluconolactons or amount of consumed oxygen.

Heretofore, for measuring the glucose concentration according to the amount of generated hydrogen peroxide a method has been adopted, in which the generated hydrogen peroxide is oxidized with a metal electrode, and the oxidizing current is measured. Alternatively, the generated hydrogen peroxide is reduced, and the reducing current is measured. However, these oxidizing and reducing currents are subject to the influence of oxygen. Further, a prior art detection electrode is liable to be influenced by changes in the surface state. Further, the principle of measurement by electrochemical means uses a sensor structure, which comprises an electrode substrate, liquid, enzyme fixed film and liquid under test. Therefore, miniaturization of the sensor is difficult due to liquid present between the electrode and the film.

As other methods for measuring the glucose concentration, there are (1) one, in which hydrogen peroxide is decomposed by catalase, and the amount of oxygen is measured, and (2) one, in which iodide ions are oxidized in the presence of enzyme (peroxidase) and inorganic catalyst (molybdenum), and the amount of iodine is measured by causing the following reaction, thereby indirectly measuring the amount of hydrogen peroxide.

$$H_2O_2 + 2I^- + H^+ \xrightarrow{\text{peroxidase}} I_2 + 2H_2O \quad (2)$$

In the above way, when measuring the glucose concentration according to the amount of generated hydrogen peroxide, the amount of consumed oxygen or amount of generated iodine is measured, and the amount of generated hydrogen peroxide is determined indirectly from the measured amount.

However, such method of measurement through two reaction stager requires a separate electrode for measuring oxygen or iodine in addition to an enzymic electrode for decomposing glucose or the like to hydrogen peroxide. In addition, the measurement is very complicated and takes a long time. Meanwhile, with the prior art electrochemical method, there are problems of contamination of the liquid under test and difficulties of miniaturization because the sensor contains inner liquid.

SUMMARY OF THE INVENTION

An object of the invention is to provide a method of manufacturing a substrate with a thin film such as a satisfactorily hydrophobic film, which is excellent in reproducibility with respect to the film composition of the thin film and orientation thereof and never causes thermal damage.

In order to attain the object of the invention, there is provided a method of manufacturing a substrate with a hydrophobic film according to the invention, which comprises a step of installing a target consisting essentially of a hydrophobic compound at a predetermined position in a reaction chamber and a step of ionizing rare gas introduced into the reaction chamber, ionizing rare gas. accelerating ions in an acceleration voltage range of 0.1 to 100 kV while converting the ions into neutral atoms, and irradiating the target with the neutral atom beam for sputtering, thereby causing growth of a hydrophobic compound on a predetermined substrate surface to manufacture a substrate with a hydrophobic film.

Generally, in a sputtering process based on a neutral atom beam, rare gas or argon (Ar) with a high sputtering factor is introduced into a reaction chamber in a vacuum (or the order of $3 \times 10^{-5}$ Torr) and ionized with a cold cathode, the ions are accelerated in a high voltage electric field and then passed through an electronic atmosphere for neutralization, and the target is irradiated with high speed neutral particles (i.e., neutral atom beam), thus forming a thin film on an intended substrate by utilizing the sputtering phenomenon.

In this sputtering process, unlike the vacuum deposition process or ion injection process utilizing the movement of energy, kinetic energy of rare gas is directly converted into kinetic energy of atoms or molecules of the target. A dense thin film thus can be formed even with high-melting materials or alloys. The neutral beam is substantially free from ions (usually containing 1% or less of ions). A beam containing ions is unsuitable because with an insulating or organic substance ions may cause chargeup, discharge or decomposition. Particularly, the sputtering process using a neutral atom beam is substantially free from ion particles. Therefore, the formation and composition of pin holes at the time of thin film formation are subject to less changes, and superior reproducibility of thin film can be obtained.

The present invention is predicated on a finding that by using the neutral atom beam sputtering process in forming a hydrophobic film of a fluorine compound or the like and controlling the beam irradiation condition, particularly accelerating voltage, it is possible to increase the content of fluorine (F) in C-F bond coupling. Thus, it is possible to approach the F/C ratio as designed. Also, heat storage of the target can be prevented by turning the target.

The accelerating voltage is suitably in a range of 0.1 to b 100 kV, preferably in a range of 1 to 10 kV. Where the voltage is below 0.1 kV, sufficient sputtering cannot be obtained with a neutral atom beam of rare gas such as argon (Ar). Where the voltage is higher than 100 kV neutralized argon or the like is injected into the target, thus reducing the efficiency of sputtering.

In a range of 0.1 to 100 kV, a desired acceleration voltage can be selected in relation to the sputtering time. Particularly, it is suitable to set the sputtering time to 60 minutes and accelerating the voltage to 8 kV. Further, for increasing the sputtering efficiency, the angle between the neutral atom beam and target surface is suitably 15° to 60°.

Further, the substrate is suitably disposed on a normal to the target surface at a point thereof bombarded by the neutral atom beam. Further, it is desired to effect parallel movement of the substrate repeatedly to obtain a homogeneous thin film.

The degree of vacuum at the time of sputtering is suitably $10^{-4}$ Torr or less. Further, the temperature is suitably in a range of $-20°$ to 60° C. Further, to prevent temperature rise due to irradiation of the target with the beam and thus prevent resultant decomposition, the target is desirably cooled down by rotating it.

The hydrophobic compound may be selected polytetrafluoroethylene, ethylene tetrafluoride-perfluoroalkylvinylether copolymer, ethylene tetrafluoro-propylene hexafluoride copolymer, ethylene tetrafluoride-ethylene copolymer, ethylene trifluoride-ethylene copolymer, ethylene trifluorochloride polymer and vinylidene fluoride polymer. Further, it is possible to use polyolefin resins such as polypropylene and polyethylene, polystyrene, polyimide, polycarbonate and hydrophobic resins having functional groups.

Another object of the invention is to provide an apparatus for manufacturing thin films, which permits formation not only of thin films of inorganic substances and multi-layer bodies, laminations and mixtures of thin films of inorganic substances but also of perfect insulating films.

To attain this object of the invention, there is provided an apparatus for manufacturing a thin film by accumulating sputtered particles on a predetermined substrate surface, which comprises a vacuum chamber, a target base provided in the vacuum chamber for holding a target material, neutral beam generation means for irradiating the target supported on the target base with a neutral beam, a substrate base for supporting the substrate and shutter means provided between the substrate base and target base for controlling the passage and blocking of sputtered particles.

In the apparatus for manufacturing a thin film according to the invention, it is suitable that a plurality of sputtering means each including neutral beam generation means, a target base and shutter means are provided such that sputtered particles generated by the individual sputtering means are collected on the substrate base, or a plurality of neutral beam generation means are provided such that the target is irradiated by neutral beams emitted from the individual neutral beam generation means, thus improving the uniformity of the film thickness distribution. Further, with the apparatus for manufacturing a thin film according to the invention, it is suitable that a substrate base drive mechanism capable of causing rotation, linear motion and arcuate motion of and/or scanning the substrate base is provided for obtaining a uniform film thickness on a predetermined substrate surface, and the substrate base is provided with substrate temperature control means.

Further, the apparatus for manufacturing a thin film according to the invention suitably comprises a first front chamber provided adjacent to the vacuum chamber, first on-off means for controlling the communication between the front chamber and the vacuum chamber, a first moving mechanism for moving the target between the vacuum chamber and first front chamber, a second front chamber provided adjacent to the vacuum chamber, second on-off means for controlling the communication between the second front chamber and the vacuum chamber and a second moving mechanism for moving the substrate base between the vacuum chamber and second front chamber. Further, it suitably comprises on-off means for controlling communication between the neutral beam generation means and the vacuum chamber.

A further object of the invention is to provide a minute ISFET sensor integrally comprising a solid-state reference FET having stable characteristics and an ISFET and a method of manufacturing the same.

In order to attain the above object of the invention, there is provided in ISFET sensor, which comprises a reference FET including a gate section and a solid film formed on the gate section and having an electrically conductive layer, a halogenated silver layer, a hydrophobic resin layer and a halide layer and generating a reference potential and an ISFET electrically isolated from the reference FET and generating an output potential or current corresponding to the concentration of ions under measurement, the concentration of ions under measurement being measured according to the output potentials or currents of the reference FET and ISFET.

With the ISFET sensor according to the invention the reference FET and ISFET are suitably formed on the same substrate. Further, it is suitable that the halide layer in the solid film contains a halide salt and that portions of the reference FET and ISFET other than the gate sections are covered with an insulating film.

Further, the ISFET according to the invention is suitably used by being mounted on an end of a catheter, and it is suitable that a temperature measurement element is provided for temperature compensation of the output potential or current according to the output of the temperature measurement element.

According to the invention, there is further provided a method of manufacturing an ISFET sensor according to the invention, which comprises a step of manufacturing a plurality of FETs by forming source and drain regions in a semiconductor substrate and forming a gate insulating film on the semiconductor substrate surface in a channel region between the source and drain regions, at least one of these FETs being used as a reference FET, the other FETs being used as ISFETS, a step of forming a conductive layer on the gate insulating film of the reference FET and a halogenated silver layer on the electrically conductive layer, and a step of forming solid film on the halogenated silver layer by successively forming a hydrophobic resin layer and halogen compound layer.

A further object of the invention is to provide an enzyme sensor, which can measure substrate concentration of glucose or the like easily, in short periods of time and accurately, is free from contamination and is capable of miniaturization, and a method of manufacturing the same.

In order to solve the above problems of the invention, there is provided an enzyme sensor, which comprises an electrically conductive substrate and a single molecule film covering at least part of the electrically conductive substrate and including an electron movement medium and enzyme.

In this enzyme sensor, electron movement reaction (i.e., oxidation/reduction reaction) in the single molecule film between enzyme and electrically conductive substrate by electron movement medium is caused to measure the enzyme reaction from changes in the electron movement reaction. The electron movement reaction is detected as changes in current at a constant active potential on the electron movement medium.

The electron movement medium and enzyme are suitably fixed in the single molecule film in a directly bonded state to one another.

The electron movement medium suitably consists of a compound having a redox center, which compound has a redox potential capable of oxidizing or reducing the active center having an active center of enzyme. Particularly where the enzyme is glucose oxidase, it is suitably a ferrocene derivative, preferably ferrocene carbonate.

The compound having a redox center may also be quinone compounds, triphosphopyridinenucleotide compounds and flavin adenine dinucleotide compounds.

As the single molecule film, to which the electron movement medium and enzyme are fixed, there may preferably be used a LB (Langumiur Blodgett) film based on the LB film. By this LB process, individual molecules are uniformly oriented on the electrically conductive substrate, and it is possible to readily form a thin film having a thickness corresponding to the length of the single molecule. Thus, the reaction taking place on the film surface can be readily transferred onto an electrically conductive substrate. More particularly, it is possible to obtain a high sensitivity sensor. Further, since the thicknesses of the individual layers of the LB film have high order properties, it is possible to form a stable lamination and readily control the film thickness and amount of enzyme in the film.

According to the invention, there is further provided a method of manufacturing an enzyme sensor according to the invention, which comprises a step of manufacturing an electrically conductive substrate, a step of forming a single molecule film with uniform molecule orientation by developing a single molecule film substance on the surface of an enzyme solution containing an electron movement medium and applying a constant secondary external pressure and a step of forming a single molecule film containing an electron movement medium and an enzyme on the electrically conductive substrate by dipping the electrically conductive substrate in an enzyme solution with the single molecule film formed on the surface.

For the formation of the single molecule film, a fatty acid, e.g., stearic acid ($CH_3(CH_2)_{12}COOH$), is used, and by dropping stearic acid on a water surface partitioned by a thin film of "Teflon" (registered trade mark), a single molecule film without satisfactory orientation is formed. By dropping oleic acid as piston oil on the other surface a pressure is applied to the "Teflon" thin plate by the diffusion force of oleic acid, thus causing movement of the "Teflon" thin plate to one water surface until equilibrium between the opposite side pressures is attained. As a result, a secondary external pressure is applied to the single molecule film of stearic acid, thus improving the orientation. By charging the single molecule film with uniform orientation onto the surface of an enzyme solution containing an electron movement medium contained in an enzyme pot, electron movement medium is adsorbed together with enzyme to the hydrophilic base side of each molecule of the single molecule film.

Therefore, by dipping the electrically conductive substrate in the solution and then raising it, a single molecule film containing the electron movement medium and the enzyme is formed on the electrically conductive substrate.

The electrically conductive substrate constitutes an electrode, and it may be manufactured by forming a metal film such as an iridium oxide ($I_rO_x$) as the electrode by means of sputtering on the glass substrate or transparent conductive glass substrate (ITO:Indian Tin oxide). However, it is possible to construct the entire substrate with a conductive material of metal or the like.

In the case of an enzyme sensor using a field-effect transistor (FET), the electrically conductive substrate may be formed on the gate section or extension of the gate section, thus permitting the miniaturization of the whole sensor including the output section.

The hydrophobic film formed by the method according to the invention having the above features has very satisfactory reproduction of film composition, film orientation and polymerization. Thus, it is possible to efficiently form a hydrophobic film having excellent insulating properties.

The substrate having a thin film thus formed can be suitably used for a reference electrode and also for SAW (surface elastic wave device) and optical waveguide.

Thus, it is possible to form a thin film without giving thermal damage to the target by irradiating the target with a neutral atom beam while rotating the target.

In the apparatus for manufacturing a thin film having the above features according to the invention, by generating a neutral beam after adjusting the beam irradiation position of the neutral beam generation means, the neutral beam bombards the target to cause the target material to be sputtered, and sputtered particles are deposited on a substrate supported on the substrate base, thus forming a thin film.

In the initial stage of sputtering, the sputtered particles may contain impurities. Thus, it is possible to form a thin film containing impurities by blocking sputtered particles with shutter means.

As is shown, according to the invention a thin film without pinholes can be readily manufactured such that it has a thickness of 1,000 angstroms or below. In addition, there is no limitation as to chemical composition such as whether it is organic or inorganic. Thus, it is possible to manufacture special performance films particularly effective for optical devices and opto-chemical devices such as superthin insulating films and artificial gratings (super-grating). Further, there are no changes in composition due to charge-up of the target, and the reproducibility is extremely improved.

Where a plurality of sputtering means, each including neutral beam generation means, a target base and shutter means are used, a laminated thin film or a multi-layer body may be readily formed by using different materials for the individual targets and sequentially on-off operating the shutter means. Further, a mixture film may be formed by opening all the shutter means at one time.

Further, by effecting the sputtering at one time with the same material used for all the targets, a thin film having a satisfactory film thickness distribution characteristics may be formed.

Further, the uniformity of the film thickness distribution may be improved by providing a plurality of neutral beam enervation means.

Further by causing rotational or linear movement of the substrate base or target base the film thickness may be made uniform over a predetermined surface portion; particular step coverage can be improved when forming a thin film on a substrate having a step. Further, the covering property of the film can be improved by providing the substrate base with heating means.

Further, by providing a plurality of targets and irradiating these targets with a beam on a time division basis, the multi-layer film and lamination film may be readily formed.

Further, by providing a first or second front chamber in the vacuum chamber and also providing a mechanism for moving the substrate base or target base, it is possible to effect replacement of substrates or targets in a short period of time. Further, by providing on-off means between the neutral beam generation means and the vacuum chamber it is possible to readily perform maintenance and inspection of the neutral beam generation means while holding vacuum in the vacuum chamber.

When the ISFET sensor having the above features according to the invention is dipped in an aqueous solution containing ions under measurement, water molecules are transmitted by permeation through the halogen compound layer or hydrophobic resin film in the solid film in the reference FET to each halogenated silver halide layer. As a result, a fixed potential is generated in the electrically conductive layer. More specifically, each halogenated silver halide layer fulfills a function corresponding to that of the reference electrolyte and reference liquid chamber in a prior art reference electrode. Thus, by using the reference FET as reference electrode it is possible to determine the ion concentration based on the output potentials or currents of the reference FET and ISFET.

As has been shown, in the ISFET sensor according to the invention, when the reference FET is formed as a solid FET by sequentially forming an electrically conductive layer, a halide compound layer, a hydrophilic resin layer and a halide compound layer as respective solid films, miniaturization is readily possible. In addition, a constant potential can be readily obtained without being influenced by pH or the like, and the stability and durability can be improved.

Further, since the reference FET and ISFET are formed integrally such that the concentration of ions under measurement can be measured on the basis of the output potentials or currents of the reference FET and ISFET, it is possible to manufacture the entire sensor as a solid, miniaturized sensor. Further, by integrating the temperature measurement element it is possible to determine temperature-compensated ion concentration, thus improving the accuracy of measurement. Further, since ah atom beam sputtering device may be used for the formation of the solid film, it is possible to form the film at room temperature, a high dimensional accuracy of pattern formation can be obtained, and mass production can be obtained by assembling the apparatus according to a semiconductor manufacture process.

In the enzyme sensor having the above features according to the invention, an electron movement medium and an enzyme are fixed in the single molecule film, and therefore the following principle can be obtained. Where the enzyme used is glucose oxidase (GOX), for instance, by using a suitable electron movement medium, flavino-adenine dinucleotide (FADH$_2$) the glucose oxidase which has become reducing type by oxidizing glucose, can be re-oxidized to the oxidizing type (FAD). Thus, enzyme can be indirectly oxidized and reduced. This phenomenon may be utilized for causing electron movement between the enzyme and the electrically conductive substrate (electrode) for directly electrochemically detecting enzymic reaction. More particularly, by using a ferrocene derivative as the electron movement medium, an electron movement from the flavin part of glucose oxidase to the electrically conductive substrate (electrode) takes place. By using ferrocarbonic acid (FCA) as ferrocene derivative, the following reaction is brought about.

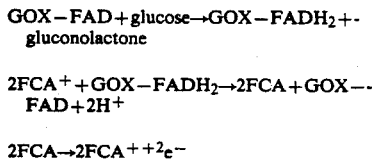

$$GOX-FAD+glucose \rightarrow GOX-FADH_2+\\gluconolactone$$

$$2FCA^+ + GOX-FADH_2 \rightarrow 2FCA + GOX-\\FAD+2H^+$$

$$2FCA \rightarrow 2FCA^+ + 2e^-$$

FIG. 24 shows the status of electron movement due to the above reaction. More particularly, with such electron movement, current in the electrically conductive substrate (electrode) is increased, and the glucose concentration can be measured from this current increase.

As has been shown, with the enzyme sensor according to the invention electron movement reaction (oxidation/reaction) by an electron movement medium is caused between the enzyme and the electrically conductive substrate in the single molecule film with uniform orientation, and the enzymic reaction is measured from changes in the electron movement reaction. Thus, it is possible to obtain accurate measurement of the enzymic reaction response in case where the substrate concentration, concealed by noise at low concentration with prior art potential response, can be measured accurately. Extremely improved response characteristics thus can be obtained. Further, the construction can be simplified, and the measurement can be extremely facilitated. Further, it is possible to reduce the measuring time.

Further, since the LB process is used for the formation of the enzyme-fixed film, it is possible to form film even if the electrode substrate is very minute in size. Since no inner liquid chamber or the like is necessary, there is no such problem as contamination of liquid under measurement. Particularly, utility as a sensor in the medical field can be extremely increased.

DESCRIPTION OF THE PREFERRED EMBODIMENTS

Now, Embodiments 1 to 4 of the invention concerning a method of manufacturing a substrate with a hydrophobic film according to the invention will be described with reference to FIGS. 1 to 5.

Embodiment 1

Figure 1:
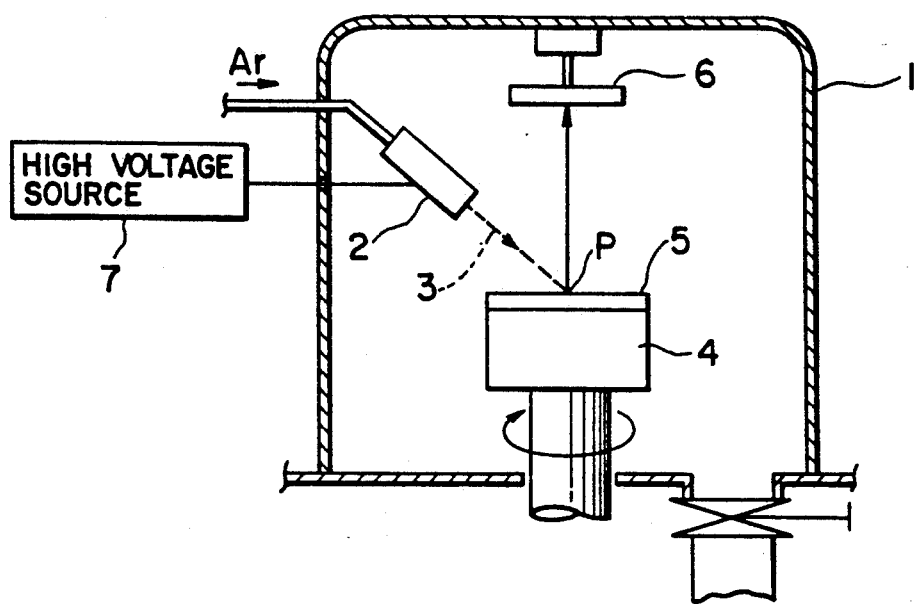
FIG. 1 is a schematic view showing a neutral beam sputtering apparatus used for various embodiments of the method of manufacturing a hydrophobic substrate according to the invention.

A thin film with a thickness of 100 to 370 angstroms was formed on a glass substrate using a neutral atom beam sputtering apparatus as shown in FIG. 1. More particularly, target 5 of polytetrafluoroethylene on turn-table 4 was irradiated with neutral atom beam 3 of argon (Ar) shot from FAB (fast atom bombardment) gun 2 in vacuum ($3 \times 10^{-5}$ Torr) at normal temperature, thus sputtering polytetrafluoroethylene molecules to grow a thin film on substrate 6 on the target irradiated with the beam at point P on normal to the turn-table.

Four different acceleration voltages of 4, 5, 6 and 7 kV were applied to FAB gun 2 from high voltage source 7, and the sputtering time was set to 60 minutes. The sputtering rate was set to 100 to 370 angstroms, and target 5 was rotated with turn-table 4 to prevent heat concentration at this time. The acceleration voltage was linearly related to the sputtering speed in a range of 5 to 8 kV.

EXPERIMENT 1

Figure 2:
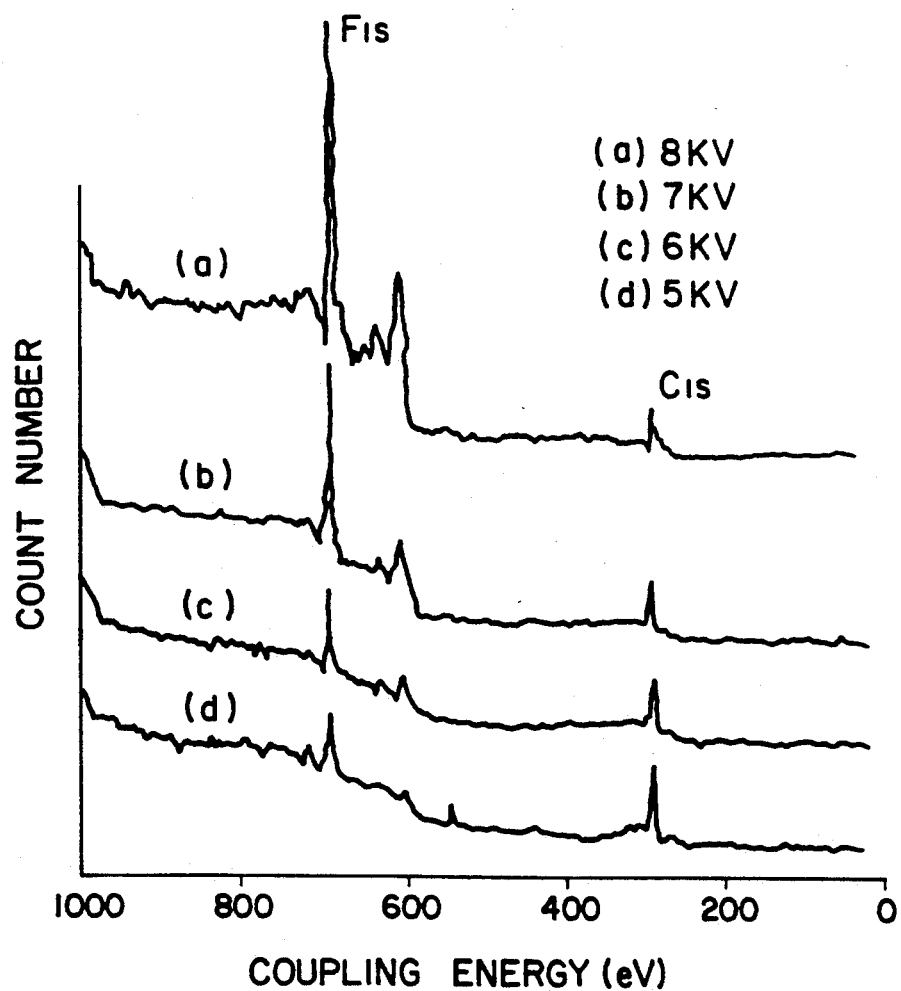
FIG. 2 is a graph showing characteristic results of analysis with ESCA in Embodiment 1.
Figure 3:
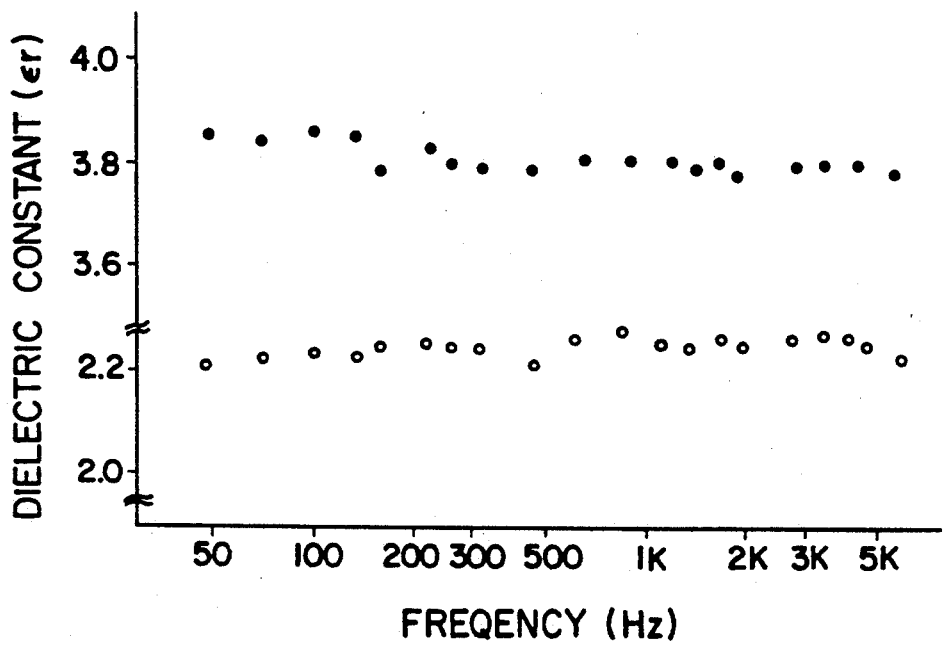
FIG. 3 is a graph showing frequency characteristic of a MIM element manufactured in Embodiment 2.

Using the results of neutral atom beam sputtering in Embodiment 1, influence of the acceleration voltage on the thin film formation was studied with respect to the four different voltages of 5, 6, 7 and 8 kV. FIG. 2 shows the results of analysis of the thin films formed with the individual voltages by ESCA (electron spectroscopy for chemical analysis).

As is shown, with the atom composition of the thin film manufactured with an acceleration voltage of 8 kV the $F_{1S}$ peak is as high as about F : C = 2 : 1 as shown in (a), while with the atom composition of a thin film manufactured with an acceleration voltage of 7 kV it is about F : C = 4 : 6 as shown in (b). More specifically, it was found that with high acceleration voltage many particles with $-(CF_2-CF_2)_n-$ were deposited, which was effective for the provision of the hydrophobic function.

Further, with the same condition of power (W) the peak current is higher with the acceleration voltages of 5 and 6 kV than with the acceleration voltages of 7 and 8 kV, and in the former case discoloring of the polytetrafluoroethylene target 5 due to carbonization was observed. This indicates that with low acceleration voltage the energy of the neutral atom beam is stored in the form of heat in target 5. It was thus found that it was necessary to avoid the temperature rise of target 5 due to bombardment energy of the neutral atom beam by increasing the acceleration voltage (about 7 or 8 kV) and increasing the sputtering speed.

EMBODIMENT 2

A polytetrafluoroethylene thin layer with a thickness of 150 angstroms was formed in the same way as in Embodiment 1 except that a metal layer was formed on a glass substrate by a deposition process and then the acceleration voltage was set to 7 and 8 kv. On this layer a metal layer with a thickness of 2,000 angstroms was formed, thus forming an MIM element consisting of metal layer, polytetrafluoroethylene thin layer and metal layer.

EXPERIMENT 2

The insulating property of the MIM element in Embodiment 2 was examined, and it was satisfactory. The low frequency dielectric characteristics were measured by using an AC impedance process (a process of measuring a dry film with an AC process: manufactured by NF circuit, lock-in amp.). The dielectric constant was measured (i.e., 3.8 with film manufactured with 7 kV and 2.2 with film manufactured with 8 kV) over a wide frequency range of 50 Hz to 5 kHz.

The dielectric strength was satisfactory, i.e., it was 4.7 kv/mm with film formed with 7 kV and 7 to 8 kv/mm with film formed with 8 kV.

EMBODIMENT 3

Sputtering was carried out with the revolution rate of polytetrafluoroethylene target 5 set at 90 minutes/rotation and the neutral beam acceleration voltage of FAB 2 to 4, 5, 6, 7, 8, 9 and 10 kV, thus forming each thin film with a thickness of about 260 angstroms on glass substrate 6.

EXPERIMENT 3

Figure 4:
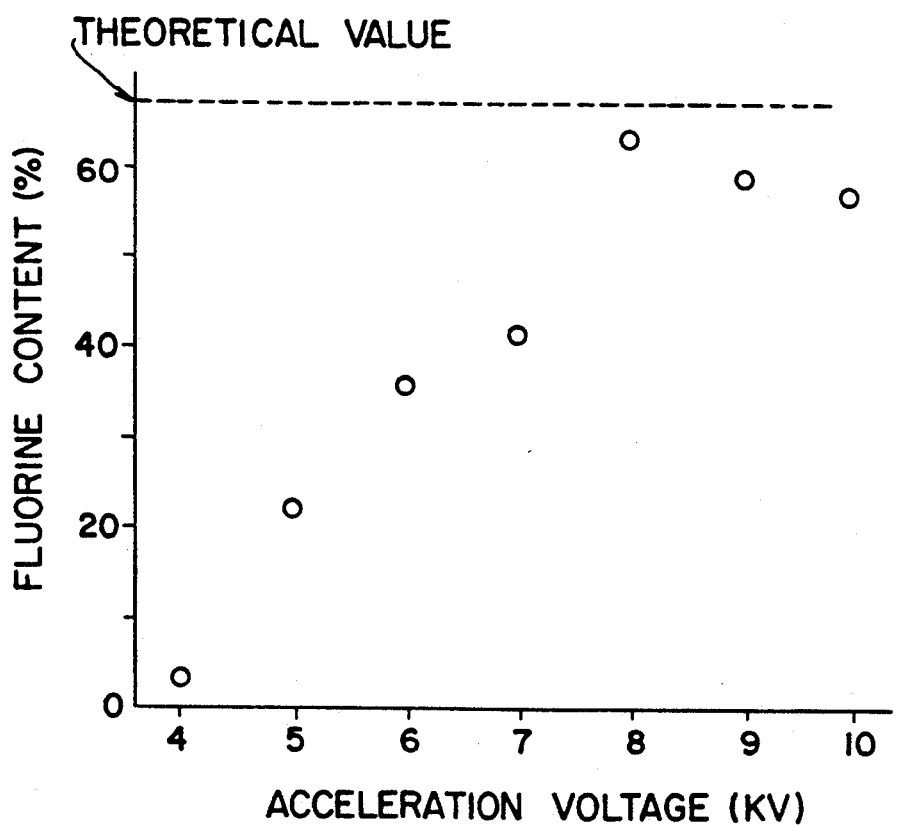
FIG. 4 is a graph showing the relation between acceleration voltage and fluorine content in thin films formed in Embodiment 3.

The fluorine content of each thin film manufactured in Embodiment 3 was calculated with ESCA, and the results are shown in FIG. 4. In the case of an acceleration voltage of 8 kV it was about 63.1% in contrast to 66.67%, which is a theoretical value of polytetrafluoroethylene (atomic number ratio).

With acceleration voltages of 9 and 10 kV, it was 60 and 58%, respectively, sufficient for the reference electrode.

With acceleration voltages of 4, 5, 6 and 7 kV the fluorine content was 3, 21, 36 and 40%, respectively, and reproducibility was inferior.

Figure 5:
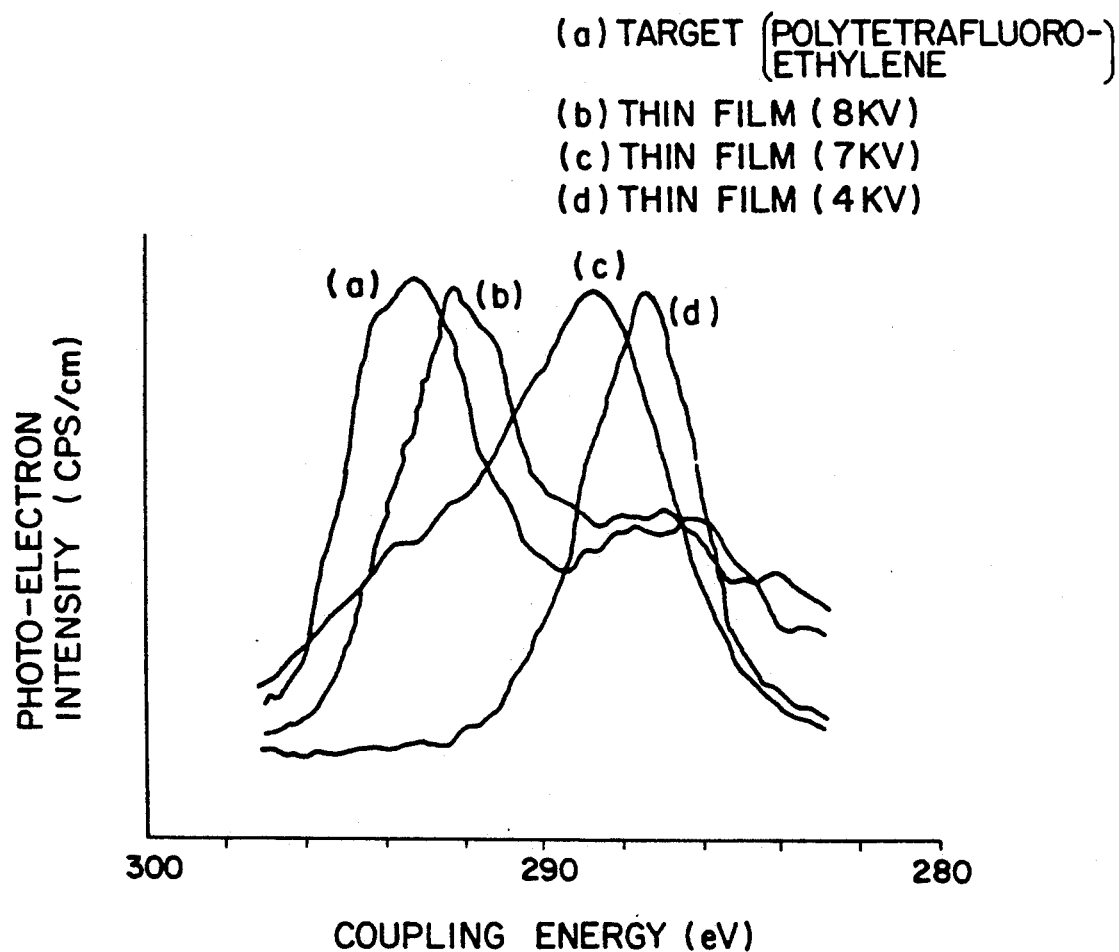
FIG. 5 is a graph showing the relation between coupling energy and photoelectron intensity in thin films manufactured in Experiment 3.

Further, as shown in FIG. 5, the ESCA peak of polytetrafluoroethylene of target 5 was as large as to correspond to $-(CF_3$ or $CF_2-CF_{22})-$. It will be seen that with sputtering effected with 8 kV it is possible to obtain bonding energy comparable to that in peak formation similar to polytetrafluoroethylene. Thus, it can be concluded that a film obtained with an acceleration voltage of 8 kv has substantially the same composition as polytetrafluoroethylene. When the acceleration voltage is reduced from 7 to 4 kV, the peak intensity corresponding to $-(CF_2]CF_{22})-$ is reduced, and the peak corresponding to coupling including $CF_2\}_n$ turns out to be increased. Therefore, it can be though that a film with large CF is formed, which is deviated from the composition of polytetrafluoroethylene.

While in the above embodiment argon (Ar) was used as the rare gas, it is possible to use krypton (Kr) and xenon (Xe) which are heavier than argon as well.

Now, Embodiments 4 to 6 of the invention concerning apparatus for manufacturing a thin film will be described with reference to FIGS. 6 to 14.

EMBODIMENT 4

Figure 6:
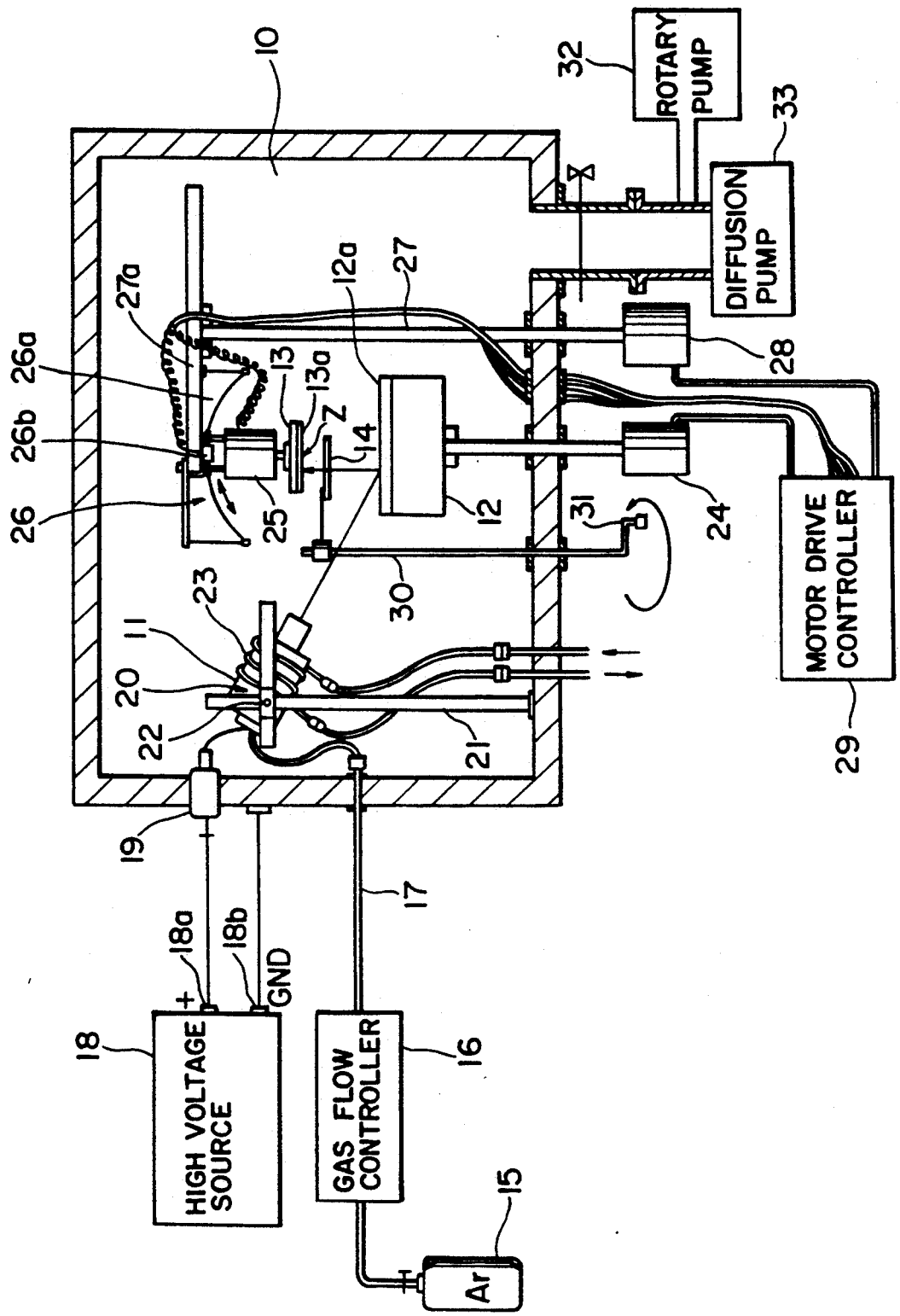
FIG. 6 is a schematic view showing the construction of Embodiment 4 concerning an apparatus for manufacturing a thin film according to the invention.

FIG. 6 is a schematic view showing the construction of an apparatus for manufacturing a thin film with a neutral atom bearing as Embodiment 4 of the invention. In the Figure, reference numeral 10 designates a vacuum chamber. In vacuum chamber 10 are disposed atom beam gun 11 for generating a neutral atom beam (manufactured by Ion Tec Co., Ltd.), target base 12 for supporting target 12a, substrate base 13 for supporting substrate 13a such as a sapphire substrate for thin film formation and shutter 14.

Outside vacuum chamber 10 are disposed gas bomb 15, which contains an inert gas such as argon gas (Ar), and gas flow controller 16. Argon gas is supplied at a predetermined rate through gas supply line 17 to atom beam gun 11. Outside vacuum chamber 10 is disposed high voltage source 18 for beam generation, with its positive terminal 18a connected to atom beam gun 11 through lead terminal 19 provided on a side wall of vacuum chamber 10.

GND terminal 18b of high voltage source 18 is grounded by being connected to a side wall of vacuum chamber 10. As high voltage source 18 there is suitably used one with a voltage range of 0 to 10 kV and maximum current of 10 MA.

Atom beam gun 11 is supported on top of support post 21 through height adjustment system 20, with the lower end of support post 21 secured to the bottom of vacuum chamber 10. Height adjustment system 20 has knob 22, permitting adjustment of the setting angle of atom beam gun 11 to adjust the atom beam irradiation angle. The outer side of atom beam gun 11 is cooled by water-cooling pipe 23.

Target base 12 and substrate supporting base 13 are disposed one above another and comprise respective turn-tables. They are driven by respective motors 24 and 25.

Motor 25 is arcuately reciprocable by an arcuate movement mechanism 26. Arcuate movement mechanism 26 comprises arcuate rail 26a and carrier 26b movable along rail 26a. On carrier 26b is mounted motor 25 for driving substrate supporting base 13.

More specifically, with arcuate movement of carrier 26b along rail 26a substrate 13a supported on substrate supporting base 13 is caused to swing, thus changing the angle, at which sputtered particles fly. Rail 26a is supported on arm 27a mounted on upper end of support post 27 which is supported vertically. Further, support post 27 is rotatable by motor 28, and rotation of motor 28 causes arcuately reciprocable movement about support post 27. The driving of motors 24, 25 and 28 and carrier 26b is controlled by motor drive controller 29.

Shutter 14 is adapted to be disposed between target base 12 and substrate supporting base 13, and it opens and closes a passage, through which sputtered particles pass, from external handle 31 through turning rod 30.

Vacuum chamber 10 is evacuated by rotary pump 32 and diffusion pump 33.

With the apparatus for forming thin film having the above construction, vacuum chamber 10 evacuated to high vacuum (to be $10^{-5}$ Torr or below) with rotary pump 32 and diffusion pump 33, high voltage is applied from high voltage source 18 to atom beam 11, and argon gas is caused to flow through gas bomb and gas flow controller 16. By so doing, gas atoms are ionized by the high voltage, and the ions thus generated are accelerated in an electric field. In the neighborhood of atom beam gun 11, the ion charges are neutralized, thus generating a high speed neutral atom beam. This neutral atom beam bombards target 12a on target supporting base 12 and thus sputters the target material, and the sputtered particles are deposited on the opposed surface of substrate 13a.

With target 12a formed such that it comprises a plurality of divisions of different materials and with target base 12 rotated at a constant rate it is possible to obtain a thin film comprising a multi-layer body. In an initial stage of sputtering the sputtered particles contain impurities, and therefore it is suitable to dispose shutter 14 between target 12a and substrate 13a for opening and closing the pass of sputtered particles. By so doing formation of a thin film containing impurities can be prevented.

The sputtered particles are ejected from the target with a cosine-curve distribution and thus have a corresponding large thickness distribution. For reducing this thickness distribution, substrate supporting base 13 may be rotated, or carrier 26b or motor 28 may be operated.

Atom beam gun 11 includes an ionizing chamber such as a cold cathode, an ion acceleration chamber and an ion neutralization mechanism. Therefore, the beam emitted from atom beam gun 11 is desirably perfectly neutralized, but several per cent (less than 5%) of the ions may remain without being neutralized.

EXPERIMENT 4

A sheet of "Teflon" (a trademark) was provided as target material on target supporting base 12, a sapphire substrate (20 mm by 20 mm by 0.5 mm) was mounted on substrate supporting base 13, and the angle between the atom beam and the horizontal surface of the target was set to 30 to 45 degrees. The position of substrate base 13 was adjusted such that sputtered particles were deposited on the sapphire substrate. Subsequently, vacuum chamber 10 was evacuated to $2 \times 10^4$ Torr or below with rotary pump 32 and diffusion pump 33. Then, the rate of argon gas flow was set to 0.5 sccm/min., argon gas was supplied to atom beam gun 11, and the voltage was increased slowly up to 8 kV to generate a neutral atom beam. Target base 12 was turned at a rate of one rotation in 30 minutes to prevent thermal decomposition of the target. Substrate supporting base 13 was rotated at a position deviated by 4 to 8 mm from a point right above the point, at which target 12a was irradiated by the neutral atom beam. Under this condition, sputtering was carried out for one hour to obtain a thin film with a thickness of 200 to 500 angstroms.

This thin film was analyzed with ESCA (Electron Spectroscopy for Chemical Analysis). As a result, peaks corresponding to $F_{IS}$ and $C_{IS}$ (C-F bonding energy) were obtained, indicating that the thin film had the same composition as "Teflon". The breakdown voltage and resistance of the Teflon thin film were measured to be 18 kv/mm or above and $10^{14} \Omega$.cm (volume resistance), respectively, indicating a highly insulating property. The dielectric constant was 2.1, close to a value corresponding to the character of Teflon.

Now, a method of improving film thickness distribution and method of improving step coverage will be described.

Figure 7:
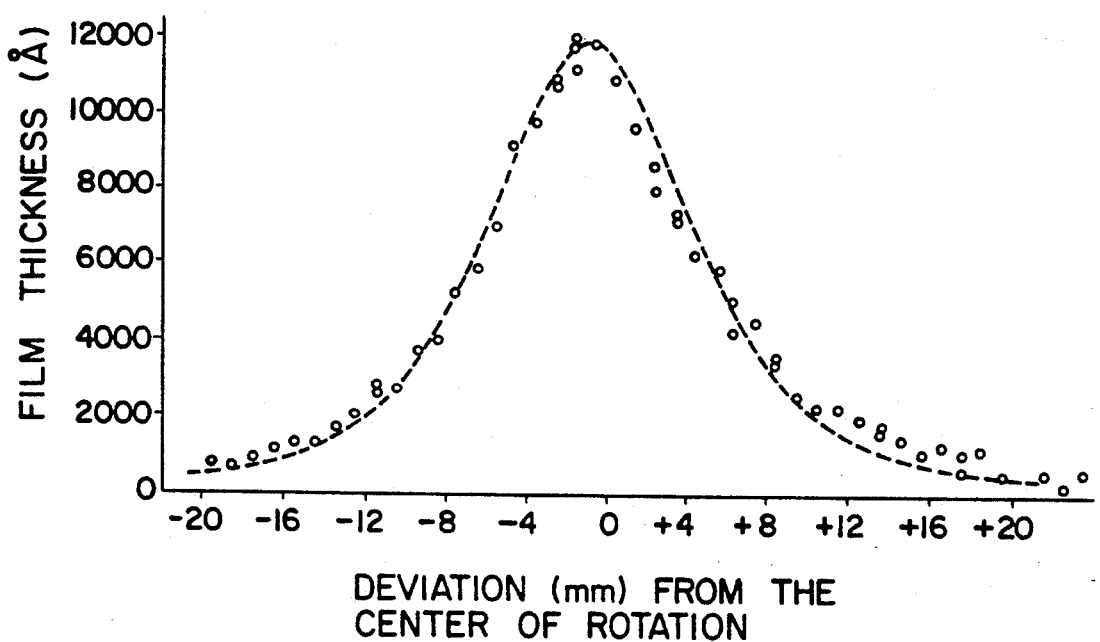
FIG. 7 is a graph showing a film thickness distribution of an atom beam gun.

As a contrast experiment, Teflon was sputtered for 4 hours under a condition of 8 kV/mA and holding substrate supporting base 13 stationary. FIG. 7 shows the film thickness distribution obtained at this time. As a result of analysis of these data, it was found that a distribution close to cos Θ (Θ: being an angle with respect to normal) holds sputtered particles which come out as a result of beam irradiation. The dashed plot represents a theoretical film thickness distribution when the cos rule is assumed.

Figure 8:
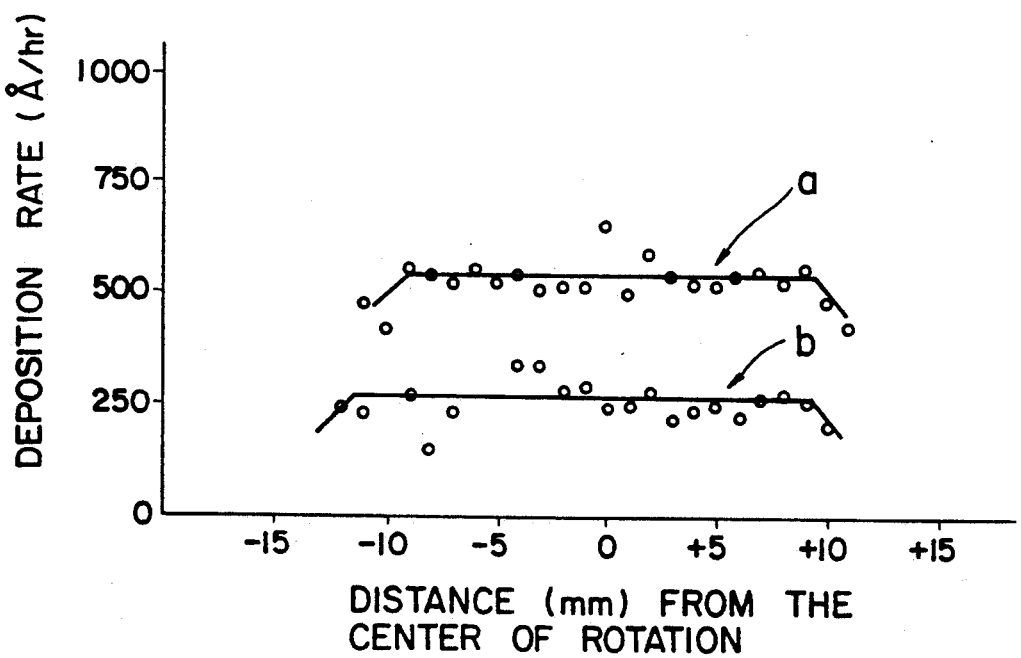
FIG. 8 is a graph showing the thickness distribution of thin films obtained with the apparatus of Embodiment 4.

The apparatus of Embodiment 4 was used to carry out sputtering for 4 hours with the distance D between substrate supporting base 13 and the target set to 10 and 20 Mm and with substrate supporting base 13 rotated at 1,000 rpm. FIG. 8 shows the film thickness distribution corresponding to sputtering for one hour in this case. The curve labeled a in the Figure corresponds to the case where D is 10 Mm, and b to the case where D is 20 mm. In both cases, the voltage condition of atom beam gun 11 was set to 7 kV/mA.

As is seen from the results, uniform film thickness is obtained within a diameter of 200 Mm. The sputtering rate was sufficiently high, i.e., 560 Å/hr.

Then, the angle of substrate 13a was set to be in a range of ±45 degrees by arcuately moving carrier 26b about the center of substrate 13a (i.e., point z in FIG. 6). Doing so permitted formation of a film on a stepped portion of the substrate indicating extreme improvement of the step coverage.

Figure 14:
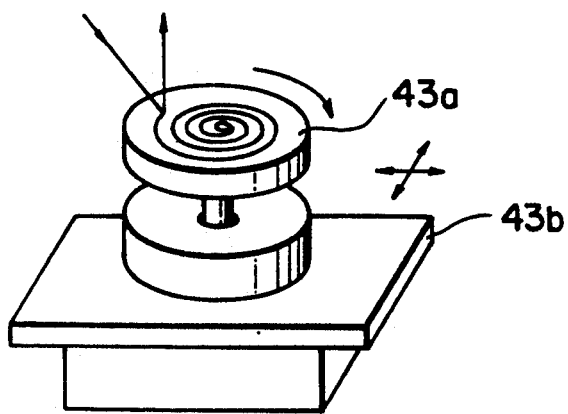

Target base 12 and substrate supporting base 13 shown in Embodiment 4 are by no means limitative; modifications as shown in FIGS. 11 to 14 may be used as well. More specifically, any structure may be used so long as it is one, in which strip-like target 12a is wound on roller 40 (FIG. 11), one, in which rod-like target 12a is moved linearly with rollers 41 (FIG. 12), an X-Y stage, preferably XYZ stage 42 (FIG. 13), or a combination of X-Y stage 43a and turn-table 43b (FIG. 14).

Where a plurality of substrates 13a are used for film formation, a planetary dome type turn-table may suitably be used.

Further, substrate supporting base 13 may be heated with a temperature control mechanism to improve the adhesion of the film. As for the temperature control mechanism, substrate supporting base 13 may be directly heated with a plate heater or the like. Alternatively, it may be heated with radiant heat energy from an infrared lamp.

As for the atom beam can, by using one which can provide unidimensional and two-dimensional array beams in addition to a single beam, it is possible to form a thin film having a uniform thickness in a broader range.

EMBODIMENT 5

Figure 9:
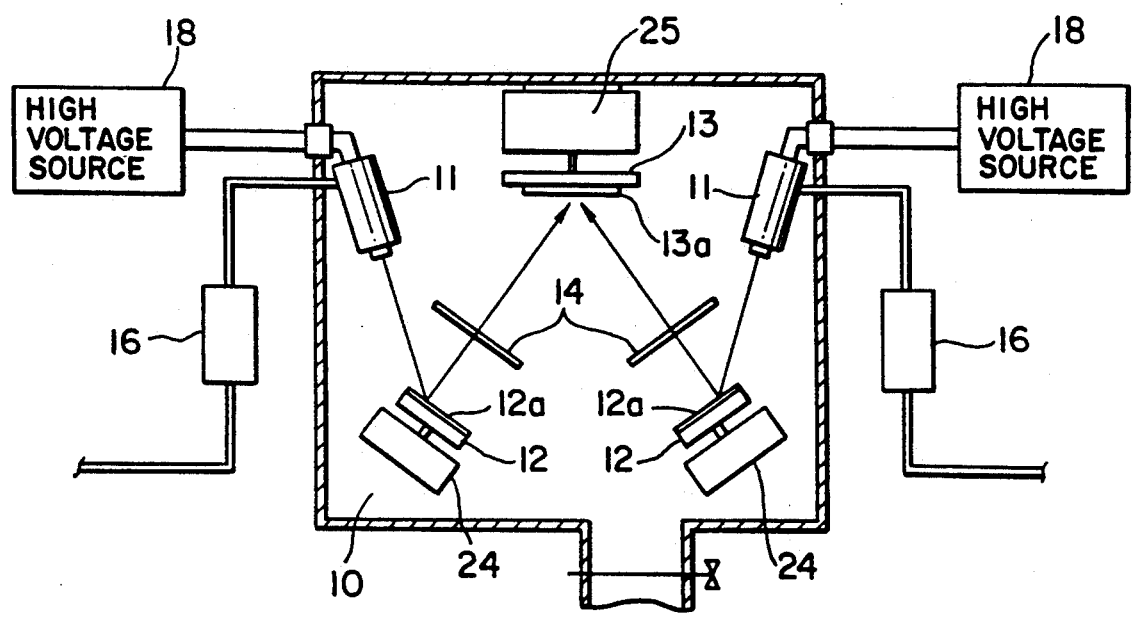
FIG. 9 is a schematic view showing an apparatus for manufacturing a thin film as Embodiment 5.

FIG. 9 is a schematic view showing the construction of an apparatus for manufacturing thin film as Embodiment 5 of the invention. In this embodiment, a plurality of, i.e., two in this embodiment, sputtering means assemblies each consisting essentially of atom beam gun 11, target base 12 and shutter 14 are provided in common vacuum chamber 10. Parts like those in Embodiment 4 are designated by like reference numerals without repetition of their description.

With this embodiment of the apparatus for manufacturing a thin film, a thin film consisting essentially of a laminated body may be manufactured by using different materials for targets 12a and sequentially on-off operating shutters 14. Further, a mixture film may be manufactured by opening all shutters 14. Further, a film having satisfactory film thickness distribution characteristics can be formed by effecting sputtering with the same material used for all targets 12a.

EXPERIMENT 5

A reference electrode was formed by using the apparatus of Embodiment 5. A Teflon plate and silver chloride (AgCl) were used for target 12a, and a laminated film with a thickness of 400 angstroms and consisting essentially of alternately laminated silver chloride and Teflon layers was formed on a thin layer of silver (Ag) formed on a sapphire substrate.

EMBODIMENT 6

Figure 10:
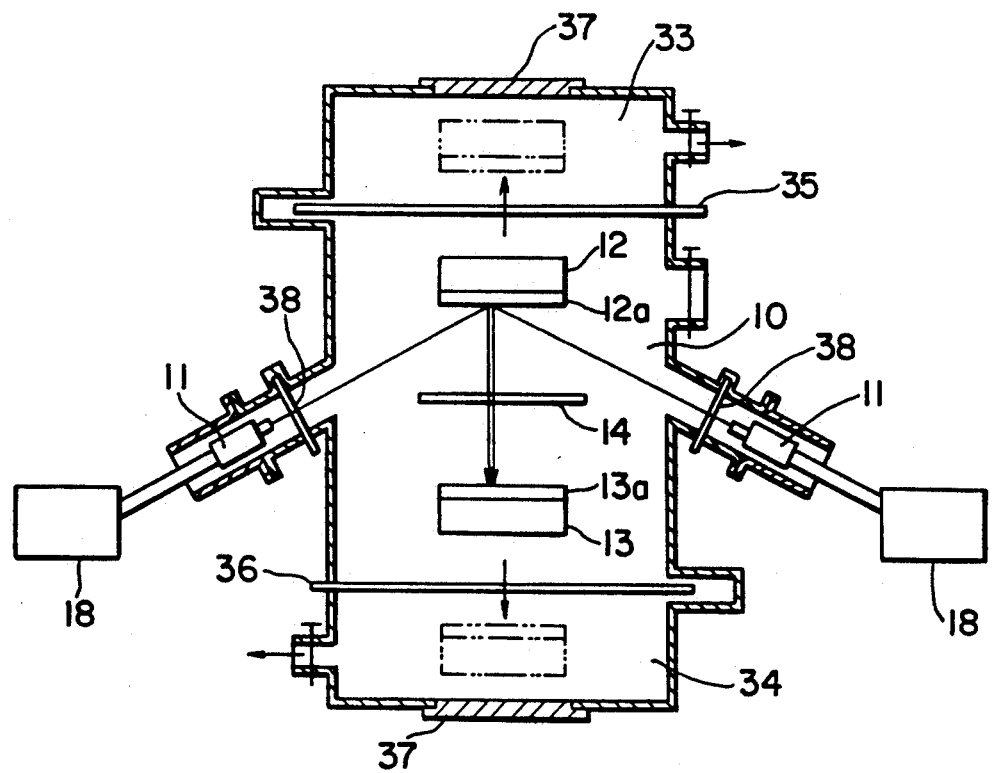
FIG. 10 is a schematic view showing the construction of an apparatus for manufacturing a thin film as Embodiment 6.
Figure 11:
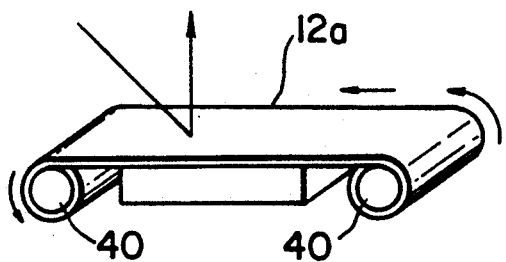
FIGS. 11 to 14 are perspective views showing modifications of the target and substrate base.
Figure 12:
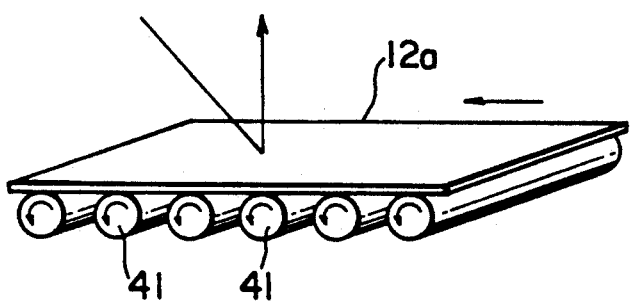
Figure 13:
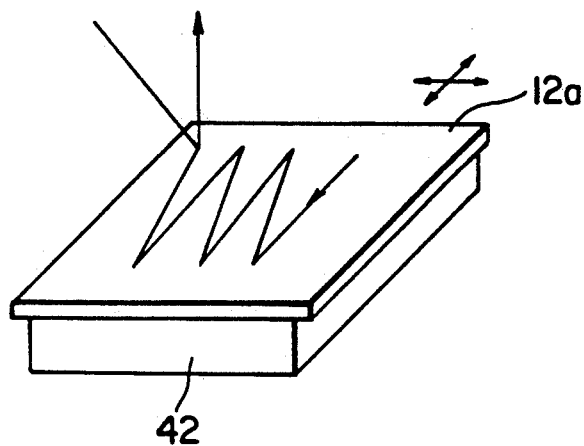

FIG. 10 shows the construction of an apparatus for forming a thin film as Embodiment 6 according to the invention. In this embodiment, front chambers 33 and 34 are formed on opposite sides of or above and below vacuum chamber 10, and valve shutters 35 and 36 are provided as on-off means between front chambers 33 and 34 and vacuum chamber 10. Further, a moving mechanism (not shown) for vertically moving target base 12 and substrate supporting base 13 is provided to permit replacement of target 12a and substrate 13a in a short period of time.

For replacing target 12a and substrate 13a, target 12a and substrate 13a are moved into front chambers 33 and 34, and then valve shutters 35 and 36 are closed. Subsequently, windows 37 are opened, and then target 12a and substrate 13a are replaced. After replacement, windows 37 are closed, then valve shutters 35 and 36 are opened, and target 12a and substrate 13a are brought back to the initial positions.

In this way, target 12a and substrate 13a can be replaced in a short period of time while holding a substantial vacuum in vacuum chamber 10.

Atom beam gun 11 is mounted on each side wall of vacuum chamber 10, and a valve shutter 38 is provided between each atom beam gun 11 and vacuum chamber 10. Thus, each atom beam gun 11 can be taken out while holding the vacuum in vacuum chamber 10.

By using the apparatus of this embodiment, target 12a can be replaced in a short period of time. In addition, uniformity of the film thickness can be improved because the system is a multi-gun system.

Further, steps involving lithography and evaluation processes during the formation of multi-layer film or lamination film, can be facilitated because substrate 13a can be readily replaced. Further, since atom beam guns 11 can be taken out while holding vacuum in vacuum chamber 10, it is possible to facilitate the maintenance of atom beam guns 11 and maintain sufficient cleanliness in vacuum chamber 10. Thus, highly pure thin film can be manufactured.

Now, an ISFET sensor as Embodiment 7 of the invention will be described with reference to FIGS. 15 to 23.

EMBODIMENT 7

Figure 15:
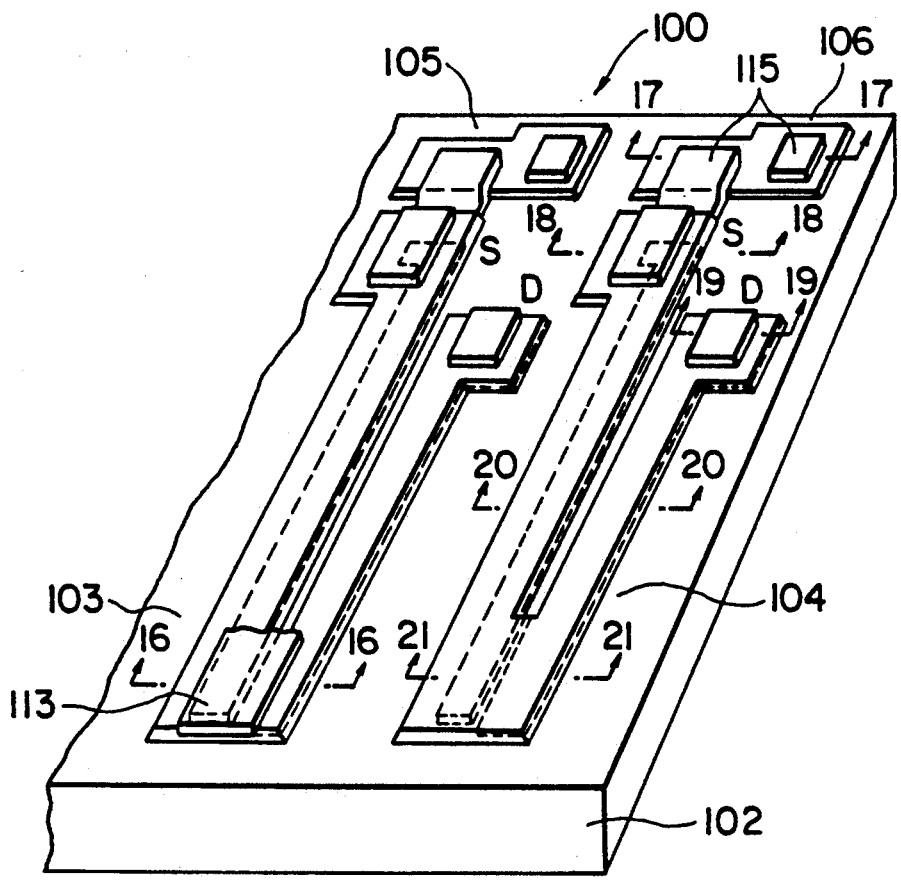
FIG. 15 is a perspective view showing the construction of ISFET sensor as Embodiment 7 of the invention.

FIG. 15 is a perspective view showing the overall construction of ISFET sensor 100 as Embodiment 7 of the invention.

In this ISFET sensor 100, reference FET 103, ISFET 104 and temperature compensation diodes 105 and 106 are formed on the surface of SOS (silicon on sapphire) substrate 102 such that they are electrically insulated from one another. Reference FET 103 serves as reference electrode, and the concentration of ions under measurement is detected according to a differential output between output potential (reference potential) of reference FET 103 and output potential of ISFET 104.

Figure 16:
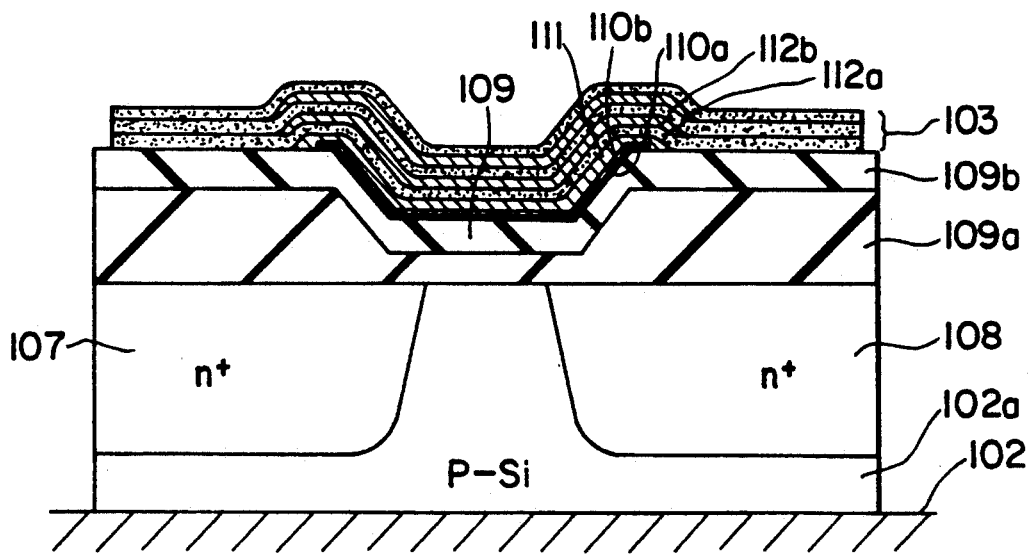
FIG. 16 is a sectional view taken along line 16—16 in FIG. 15.
Figure 17:
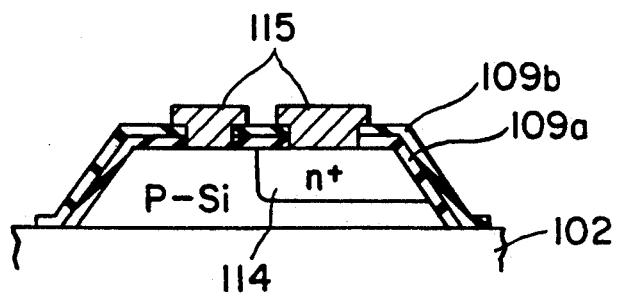
FIG. 17 is a sectional view taken along line 17—17 in FIG. 15.
Figure 18:
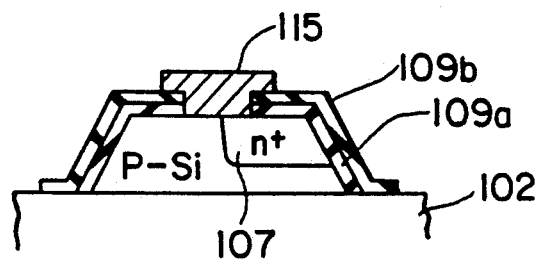
FIG. 18 is a sectional view taken along line 18—18 in FIG. 15.
Figure 19:
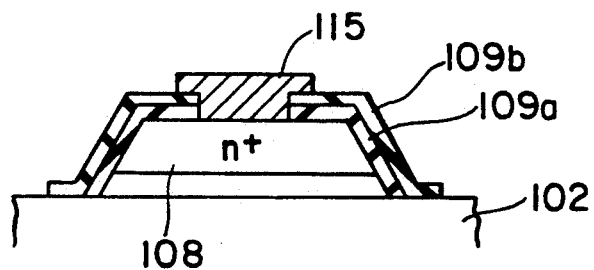
FIG. 19 is a sectional view taken along line 19—19 in FIG. 15.
Figure 20:
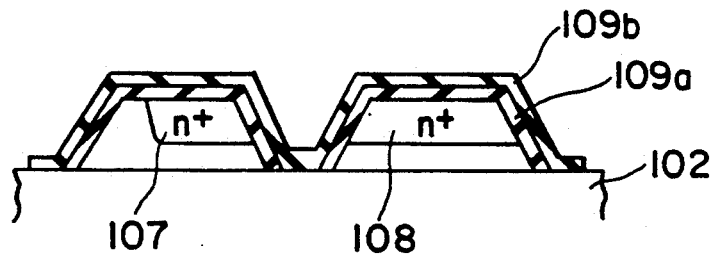
FIG. 20 is a sectional view taken along line 20—20 in FIG. 15.
Figure 21:
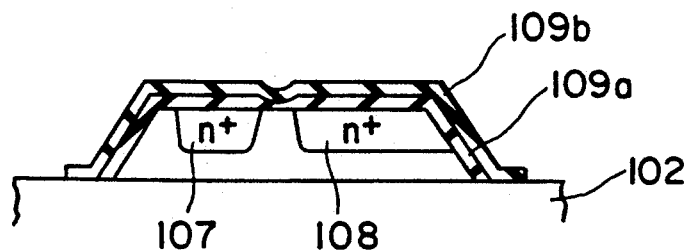
FIG. 21 is a sectional view taken along line 21—21 in FIG. 15.

FIG. 16 shows sectional structure of reference FET 103. Source and drain regions 107 and 108 are formed by diffusion of n-type impurity, e.g., arsenic (As), in silicon layer 102a on SOS substrate 102. On a channel region between regions 107 and 108 is formed gate insulating film 109 consisting of silicon oxide ($SiO_2$) film 109a and silicon nitride ($Si_3N_4$) film 109b. on gate insulating film 109 is formed an electrically conductive layer consisting of a chromium (Cr) layer 110a and silver (Ag) layer 110b. On silver layer 110b is formed silver chloride (AgCl) layer 111 such as to cover the entire surface of silver layer 110b. Further, on silver chloride layer 111 is formed lamination film 113 consisting essentially of alternate lamination of thin films of a hydrophobic resin, e.g., thin films 112a of polytetrafluoroethylene (PTFE), and silver chloride thin films 112b containing sodium chloride (NaCl). By arranging the layers such that the uppermost layer is polytetrafluoroethylene thin film 112a so that silver chloride thin films 112b are not exposed to the outside, no end portion of lamination film 113 will be attacked by chlorine ions.

Although not shown on the side of ISFET 104, an ion-sensitive film is formed. FIGS. 17 to 21 show sectional structures of various parts of the structure shown in FIG. 15.

ISFET sensor 100 is manufactured in the following way. First, silicon layer 102a with a thickness of about 6,000 angstroms was patterned to an island form on SOS substrate 102 by wet etching using hydrazine as etching liquid. Then, arsenic ions ($As^+$) were selectively implanted in a concentration of 1 to $5 \times 10^{15}$ atm/cm$^2$ at 100 key while forming PN junction 114 between diodes 105 and 106 by using an ion implantation unit (UIAVC, IXK-7000). Then, silicon oxide film 109a with a thickness of 1,000 angstroms was formed by thermal oxidation on gate sections of reference FET 103 and ISFET 104. Then, silicon nitride ($si_3N_4$) film 109b with a thickness of 1,500 angstroms was formed by using a thermal CVD (chemical vapor deposition) process.

Then, contact holes were formed in correspondence to source and drain regions 107 and 108 and anodes and cathodes of diodes 105 and 106. Then, electrode 115 consisting essentially of a chromium layer with a thickness of 500 angstroms and a copper layer with a thickness of 2 microns was formed in each of the contact holes. The contact holes were opened such that source region 107 of each FET was short-circuited to the substrate. Further, the electrode was formed such that source electrode and anode electrode of diode were connected to each other.

Then, chromium layer 110a with a thickness of 50 to 200 angstroms was formed by the vacuum deposition process on gate insulating film 109 of reference FET 103 shown in FIG. 16 through a first metal mask. Then, silver layer 110b with a thickness of 1,000 to 2,000 angstroms was deposition formed, and then the first metal mask was replaced with a slightly greater second mask, and silver chloride layer 111 with a thickness of 200 to 300 angstroms was formed such as to cover the entire surface of silver layer 110b.

Then, the mask was replaced with a further greater third mask, and sputtering was carried out for one hour by using an argon atom beam sputtering apparatus and with polytetrafluoroethylene (PTFE) as target under conditions of acceleration voltage of 8 kV and current of 1.0 mA to form polytetrafluoroethylene thin film 112a with a thickness of about 200 to 300 angstroms. Subsequently, the mask was replaced with the second metal mask, and silver chloride layer 112b with a thickness of 200 to 300 angstroms and containing 1 to 100 mol% of sodium chloride (NaCl) was formed using a vacuum deposition process. Then, polytetrafluoroethylene thin film 112a with a thickness of 200 to 300 angstroms was formed by sputtering in the same way as described above.

In this way, reference FET 103 was manufactured, which consists of laminated film 113 obtained by alternatively forming polytetrafluoroethylene thin films 112a and silver chloride layers 112b containing sodium chloride.

Subsequently, contact electrodes were silver paste connected using leads constituted by a copper layer print pattern formed on a flexible substrate made of a polyimide material. Then, ISFET 104 and reference FET 103 were covered except for gate sections with an insulating film consisting essentially of a polyimide resin and a silicone resin for electric insulation.

Figure 22:
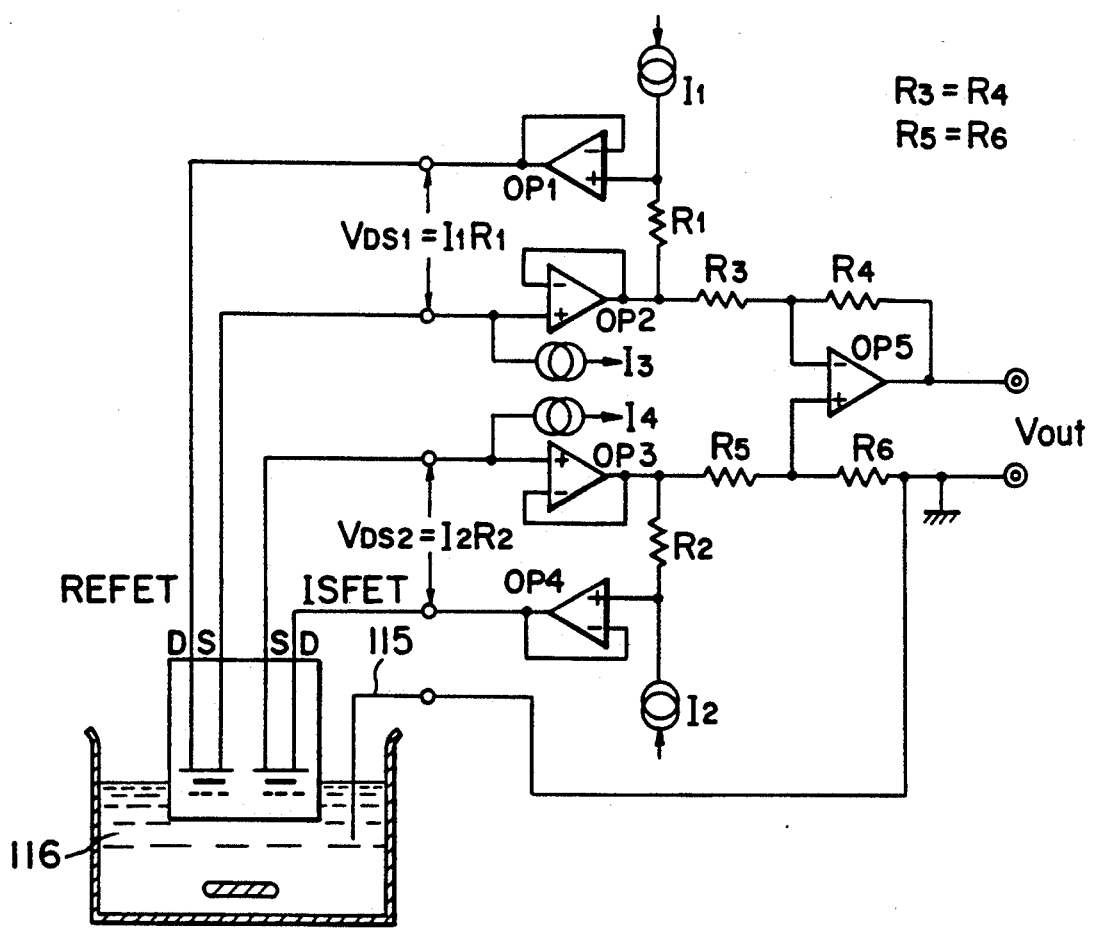
FIGS. 22 and 23 are circuit diagrams showing respective ISFET drive circuits.

As a driver for ISFET sensor 100 manufactured in the above way there may be used one as shown in FIG. 22, including differential amplifiers OP1 to OP5, constant current sources $I_1$ to $I_4$ and resistors $R_1$ to $R_6$. This circuit is used as source follower to drive reference FET 103 and ISFET 104 as constant current sources $I_3$ and $I_4$ and constant voltage sources $V_{DS1}$ and $V_{DS2}$ in a floating state. The output of this source follower is amplified by differential amplifiers OP1 to OP5 and provided from output terminal $V_{OUT}$. In this way, a potential difference between ISFET 104 and reference FET 103 can be obtained to obtain the ion concentration of subjected liquid 116 under test.

In this case, by manufacturing ISFET 104 and reference FET 103 in the same process, their threshold voltages and drifts may be made the same. Further, by a differential output it is possible to obtain stable and highly accurate measurement. In this case, however, it is necessary to dip common electrode 115 with the sensor for electric grounding (i.e., potential setting) of differential amplifiers OP1 to OP5. Common electrode 115 may be formed by using a metal which is only corroded with difficulty, such as platinum (Pt), gold (Au), nickel (Ni), titanium (Ti) and tungsten (W).

EXPERIMENT 7

ISFET sensor 100 manufactured in Embodiment 7 was connected to the ISFET drive circuit as shown in FIG. 22 and then dipped in subject liquid under test to measure the output potential ($V_{OUT}$) by varying the pH. As a result, a satisfactory linear relation was shown at 25° C. in a pH range of 2 to 10, the slope of the line being 50 to 60 mV/pH corresponding to ideal sensitivity (equation of Nernst). Further, it was found that the response time at this time was very short, i.e., within one second.

EXPERIMENT 8

Figure 23:
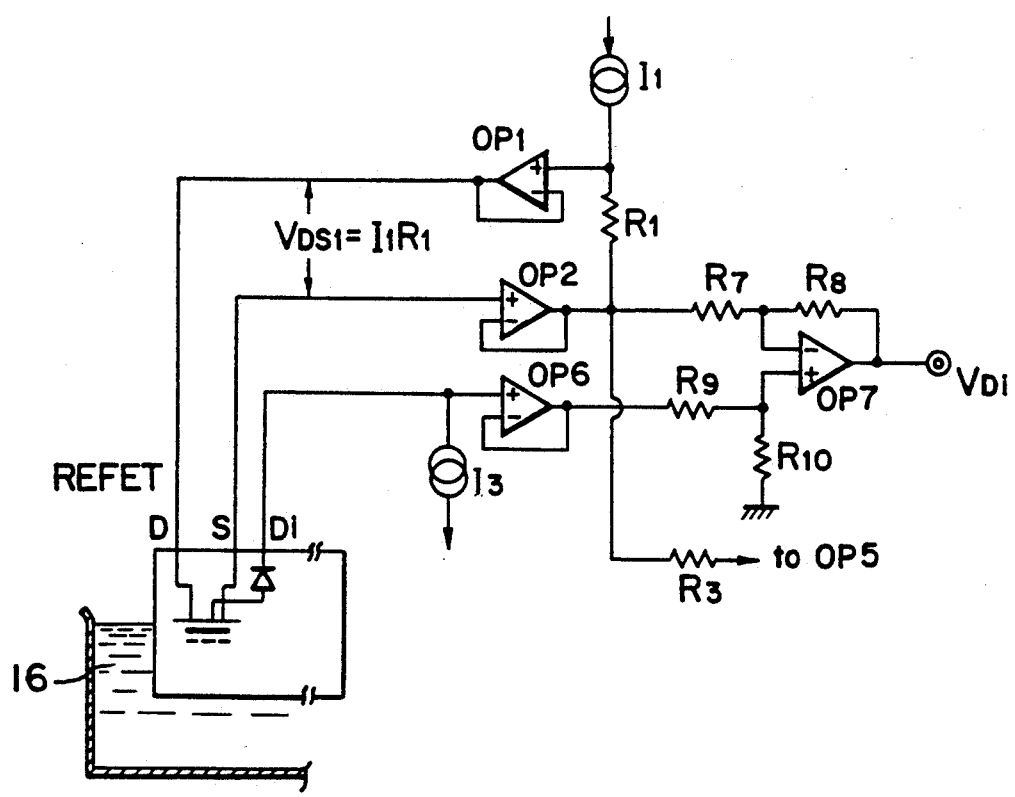

ISFET sensor 100 manufactured in Embodiment 7 was modified to obtain an ISFET driver circuit as shown in FIG. 23, which could measure the forward potential difference of diodes 105 and 106. Using this circuit, temperature characteristics of output voltage $V_{Di}$ and temperature were in a linear relation to each other in a temperature range of 0° to 50° C. The slope was found to be 1.8 to 2.8 MV/° C. The circuit construction on the side of ISFET 104 is the same as shown in FIG. 22, so it is not shown in FIG. 23.

From the above, it was found that with the ISFET sensor of this embodiment the ion concentration could be measured in a temperature-compensated state for the electromotive force and temperature could be measured simultaneously from, respectively, the output potential of reference FET 103 and ISFET 104 and from the output potential $V_{Di}$ of diodes 105 and 106.

While the invention is shown in conjunction with Embodiment 7, this embodiment is by no means limitative, and it can be modified variously without departing from the scope of the invention. For example, while in the above embodiment the ion concentration is detected from the output potential of FETs 103 and 104, it may be detected from the output current as well.

Now, enzyme sensors as Embodiments 8 and 9 of the invention will be described with reference to FIGS. 24 to 27.

Figure 24:
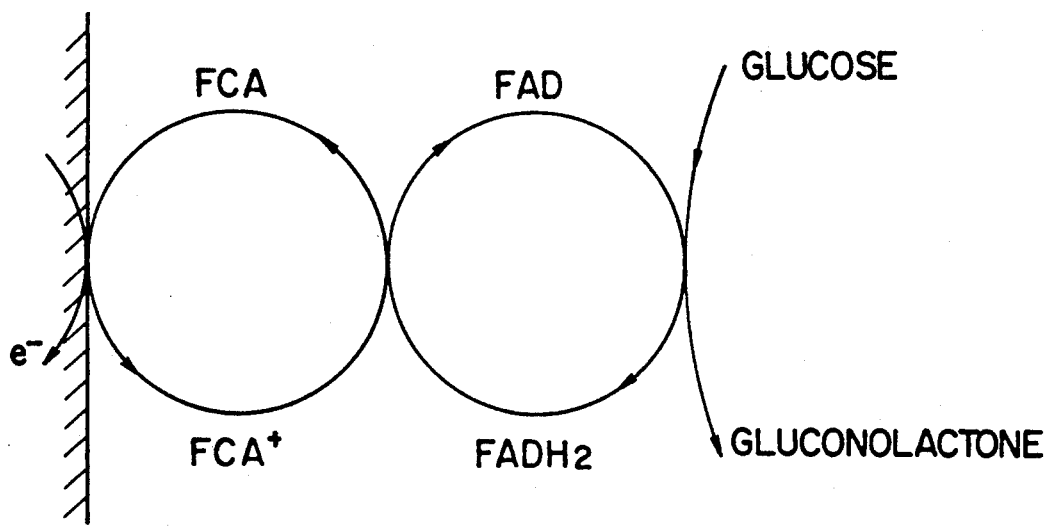
FIG. 24 is a schematic view showing the status of electron movement in an enzyme sensor according to the invention.

The status of electron movement has already been described with reference to FIG. 24.

EMBODIMENT 8

Figure 25:
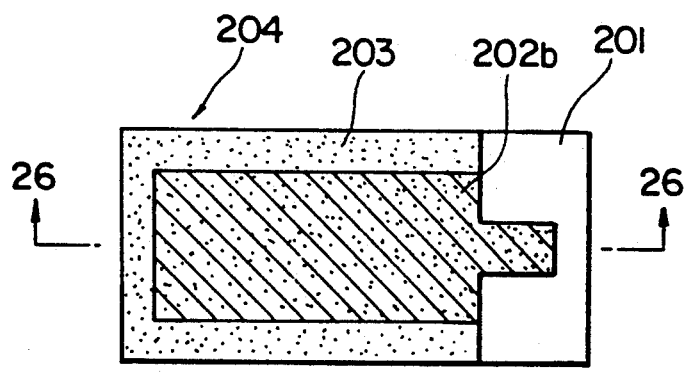
FIG. 25 is a plan view showing the construction of an enzyme sensor as Embodiment 8 of the invention.
Figure 26:
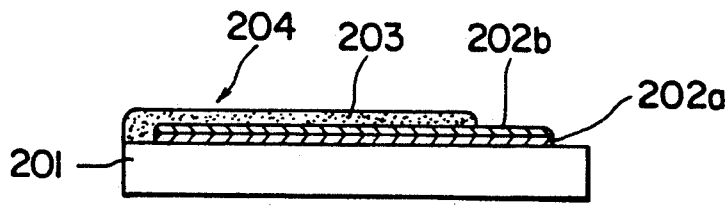
FIG. 26 is a sectional view taken along line 26—26 in FIG. 25.

Glass plate 201 (15 Mm by 5 Mm by 1.2 Mm) as substrate as shown in FIGS. 25 and 26, was washed with an acetone-methanol blend solution by supersonic wave, then washed with water and then dried. Then, using a high frequency sputtering apparatus ("SPF-210H", Nichiden Anerver Co., Ltd.), iridium oxide film 202a with a thickness of 1 micron was formed on glass plate 201 under conditions shown below. Platinum thin film 202b with a thickness of about 0.1 micron was further formed on iridium oxide film 202a to obtain an electrically conductive substrate 204 (electrode).

| Iridium oxide film | Oxygen pressure | $2 \times 10^{-2}$ Torr |
|---|---|---|
| | Sputtering power | 20 W |
| | Film formation speed | 8.5 Å/min |
| Platinum film | Argon gas pressure | $8 \times 10^{-2}$ Torr |
| | Sputtering power | 50 W |
| | Film formation speed | 68 Å/min |

Figure 31:
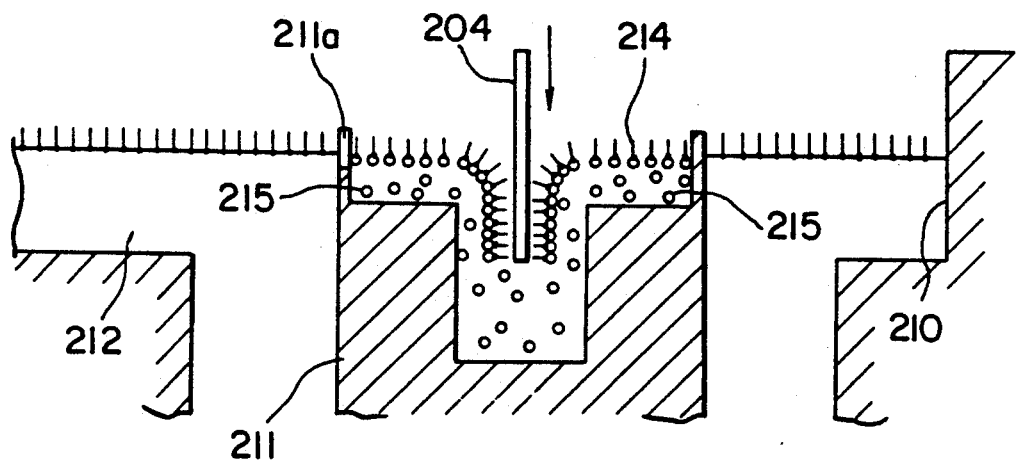
FIG. 31 is a schematic view showing the formation of LB film.

Now, using a LB film manufacturing apparatus shown in FIGS. 27 to 30, LB film 203 with fixed enzyme and electron movement medium (single molecule film) was formed on the surface of electrically conductive substrate 204. FIG. 31 schematically shows the status of formation of LB film.

Enzyme pot 211 was put into a deep portion of water tank 210 with Teflon coating provided over the entire surface. Lower liquid layer 212 obtained by dissolving barium chloride ($BaCl_2$) and potassium hydrocarbonate ($KHCO_3$) in pure water was charged to the outside of pot 211, while an enzyme solution containing electron movement medium was charged to the inside of pot 211. The inside and outside of enzyme pot 211 were communicated only by notch 211a so as to prevent leakage of inner enzyme to a certain extent. Barium chloride was incorporated in lower liquid layer 212 in order to form a stable film by reaction with stearic acid to- be described later. Potassium bicarbonate is provided for adjusting the pH of the water phase.

Figure 27:
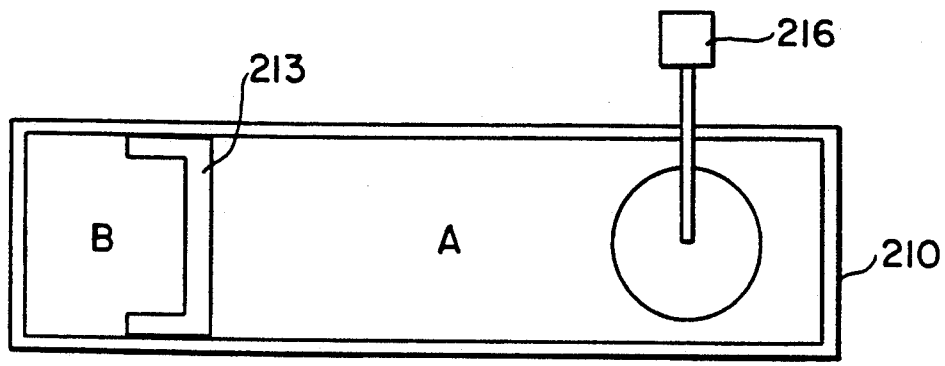
FIG. 27 is a plan view showing an apparatus for manufacturing a LB film.

As shown in FIG. 27, partitioning plate 213 made of Teflon is floated on the water surface in water tank 210 as shown in FIG. 27, thus partitioning the water surface into two regions A and B.

A stearic acid solution was dropped as single molecule substrate onto water surface A of enzyme pot 211 to develop a single molecule film over water surface A, while dropping a slight amount of oleic acid onto water surface. As a result, with diffusion of oleic acid, partitioning plate 213 was pushed until an equilibrium is set up between water surfaces A and B. Thus, secondary external pressure is applied to single molecules of stearic acid, thus improving the orientation of molecules relative to one another. Since the inside and outside of enzyme pot 211 are communicated by notch 211a, single molecule film 214 with good orientation property is formed on the inner surface as well. The hydrophilic base side of single molecule film 214 adsorbs enzyme-ferrocene coupling substance 215 in enzyme pot 211. In this state, by lowering electrically conductive substrate 204 into enzyme pot 211 and gradually raising it, a single molecule film with good orientation property is formed on the surface of platinum thin film 202a.

The above operation was repeated to laminate (one to seven) films with enzyme-ferrocene coupling substance 215 adsorbed thereto on electrically conductive substrate 204 to form LB film 203, thus forming glucose sensor.

The enzyme solution was prepared in the following way.

A solution is obtained by dissolving 400 mg of glucose oxidase, 40 mg of ferrocene carbonic acid, 2 mg of cyanamide (coupler) and 3603.6 mg of urea (coupler) in 10 ml of phosphoric acid buffering liquid (PH=6.86), and it was put into a cellophane water sack and then held dipped in water for a couple of days. In this way, dialyses of urea is effected to manufacture enzyme-ferrocene coupling substrate 215.

Figure 28:
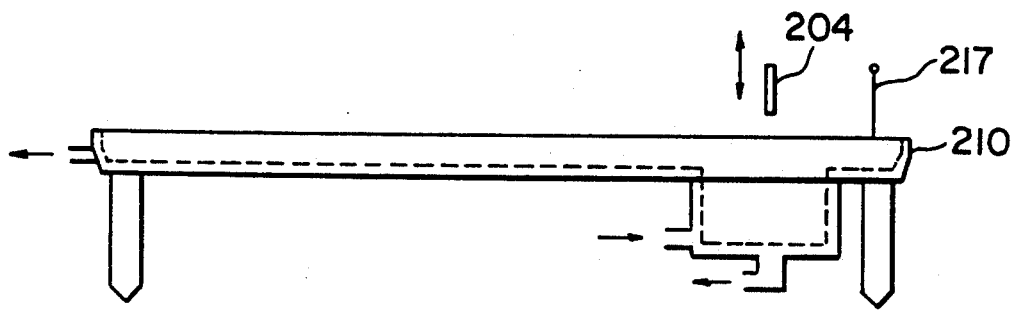
FIG. 28 is a side view showing the same apparatus.
Figure 29:
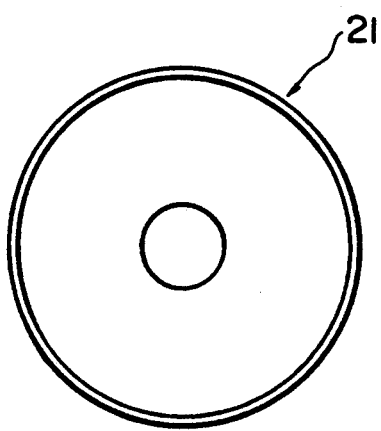
FIG. 29 is a front view showing an enzymic pot.
Figure 30:
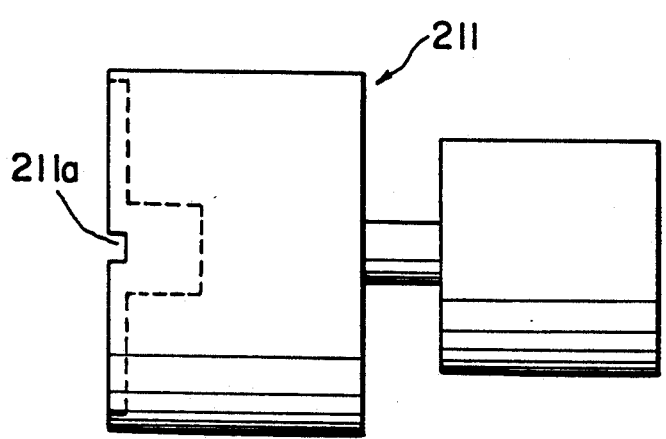
FIG. 30 is a side view showing the same enzymic pot.

In FIG. 27 reference numeral 216 designates LB film extractor, and in FIG. 28 reference numeral 217 designates a surface pressure gauge, and the arrow shows the temperature-controlled water circulation path.

CONTRAST EXAMPLE 1

Glucose sensor was manufactured in the same way as in Embodiment 8 except that no ferrocene carbonic acid was incorporated in the enzyme solution.

EXPERIMENT 9

Figure 32:
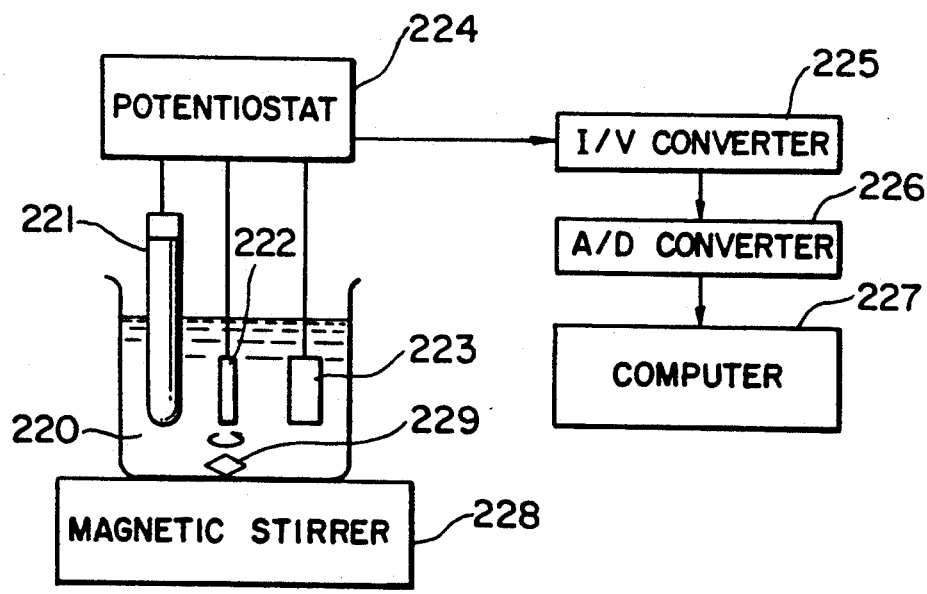
FIG. 32 is a schematic view showing an apparatus for measuring current.
Figure 33:
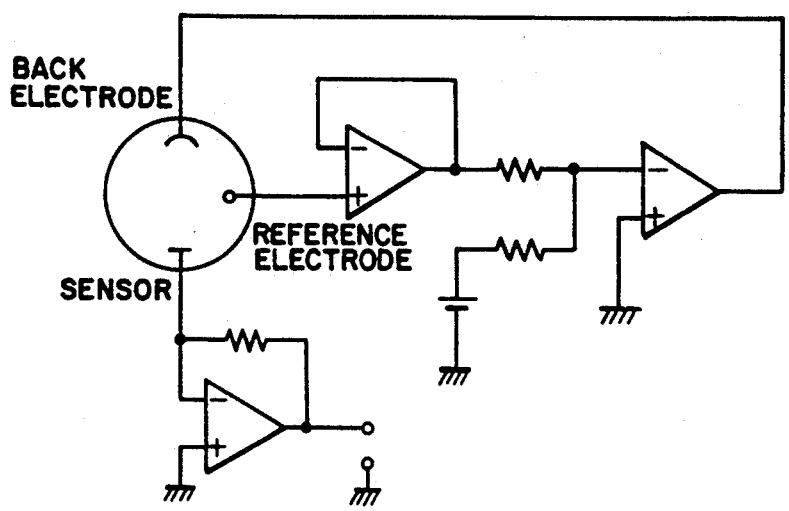
FIG. 33 is a circuit diagram showing a potentiostat.

Sensors 223 manufactured in Embodiment 8 and Contrast Example 1 were dipped as an active electrode in solution 220 for a test of the current measurement system shown in FIG. 32, and output current of sensor 223 was measured with reference electrode 221 (sodium chloride calomel electrode) and back or counter electrode 222 (platinum electrode). More specifically, while holding the electrode potential constant (0.3 to 0.6 V) with potentiostat 224 (constant potential unit) having a specific circuit construction shown in FIG. 33, a signal from sensor 223 was supplied through potentiostat 224 to current (I)-voltage (V) converter 225 for conversion to voltage, which was then converted in analog (A)-to-digital (D) converter 226, and digital signal thus obtained was supplied to a computer 227. During measurement, agitator 229 is rotated with magnetic stirrer 228, thus agitating solution 220 under test.

Figure 34:
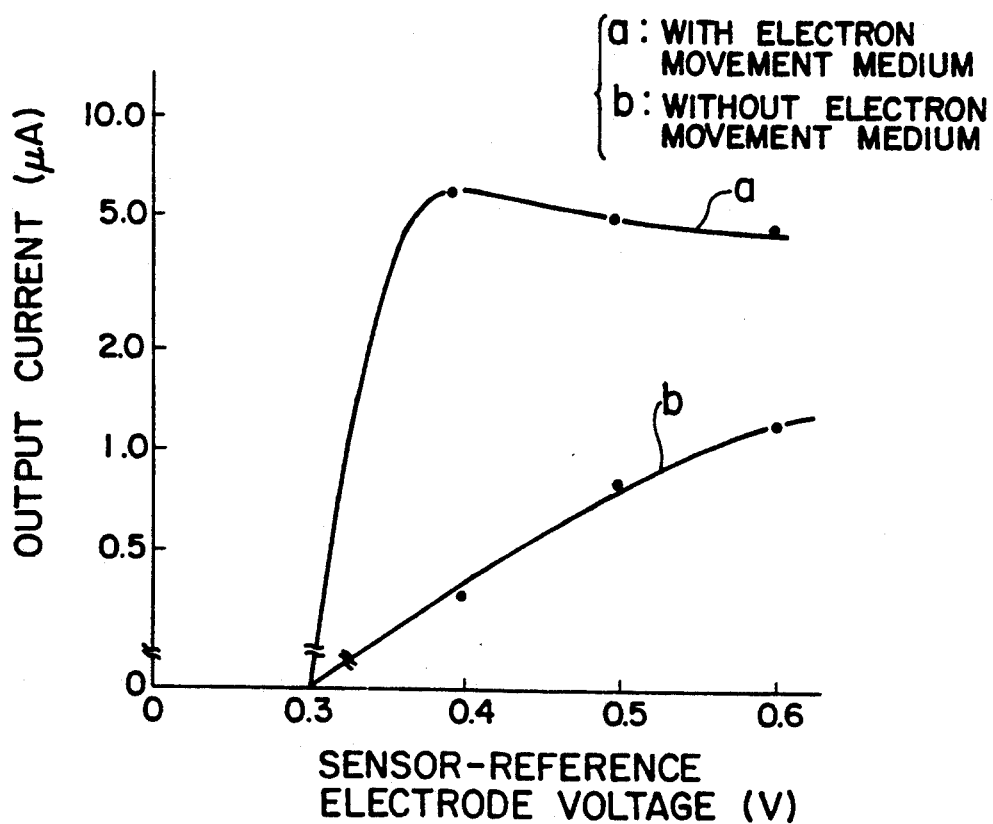
FIG. 34 is a graph showing the relation between sensor reference electrode voltage and output current.

FIG. 34 shows output currents with different potential difference between sensor 223 and reference electrode 221.

With the sensor of Embodiment 8, the greatest output current (about 5.0 gA) could be obtained at 0.4 V. In the case of the sensor without ferrocene carbonic acid in Contrast Example 1, output current increased gradually up to 0.6 V. But, the output current was 0.1 1μA even at 0.6 V. It is found that the addition of ferrocene carbonic acid to the electron movement medium was greatly effective.

EMBODIMENT 9

A glucose sensor was manufactured in the same manner as in Embodiment 8 except for that LB film 203 of the sensor of Embodiment 8 was formed such that it consisted essentially of five layers.

EXPERIMENT 10

Figure 35:
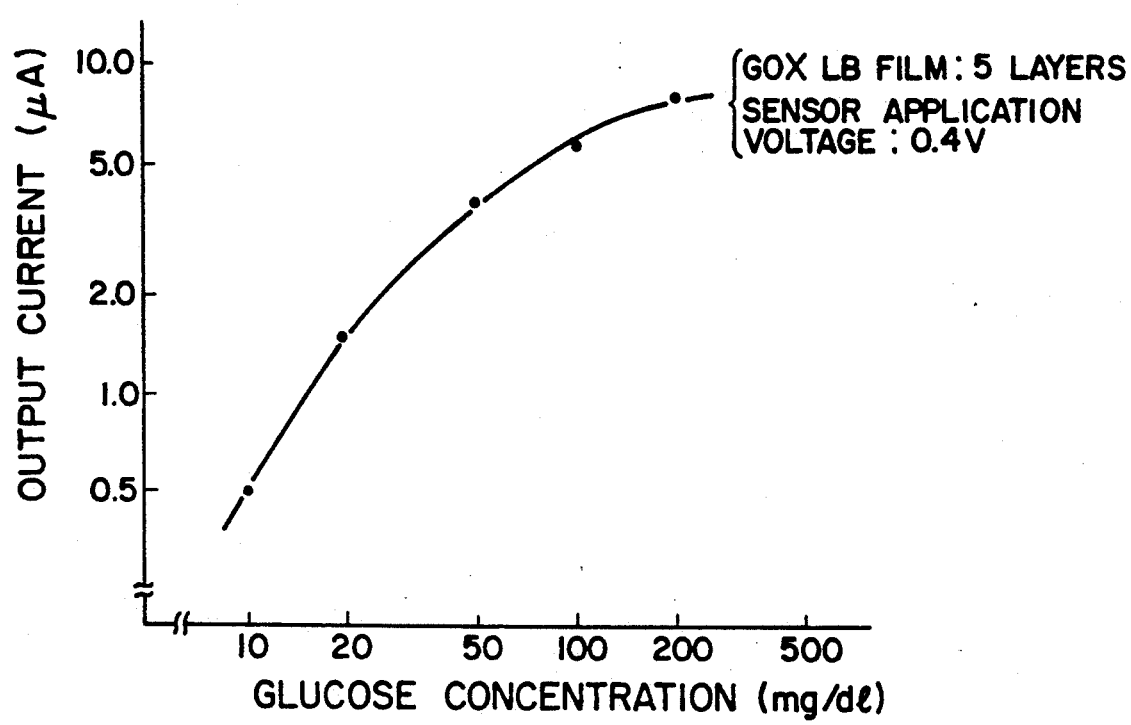
FIG. 35 is a graph showing the relation between glucose concentration and output current.

Using the apparatus shown in FIG. 32, changes in output current were measured in the cases of glucose concentrations 10, 50, 100, 200 and 500 mg/dl. FIG. 35 shows the results. The output current changed linearly for glucose concentrations less than 50 mg/dl, but a converging curve resulted for higher glucose concentrations.

Further, after de-oxidizing carried out by causing bubbling of nitrogen gas in the cell shown in FIG. 32, the output current change with the glucose concentration was measured in the same way as described above. It was found that no less than about 80% of current shown in FIG. 35 was caused, and a satisfactory linear relationship was obtained for glucose concentrations less than 50 mg/dl. It was thus found that the enzyme sensor according to the invention could be used even without oxygen.

Figure 36:
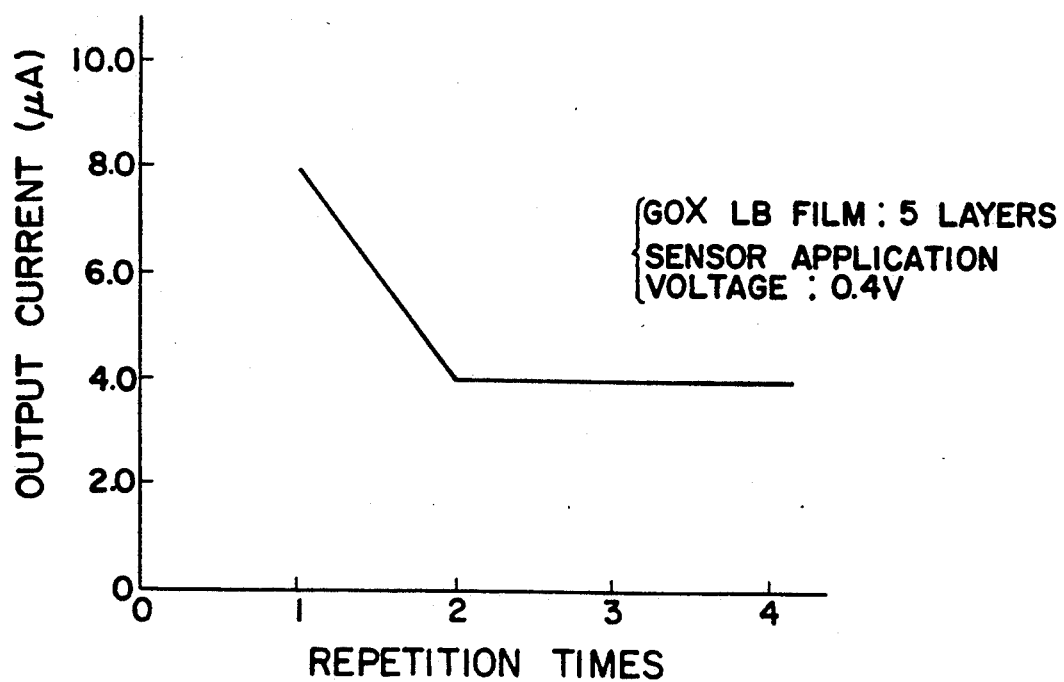
FIG. 36 is a graph showing a reproduction characteristic of the sensor.

FIG. 36 shows results of reproducibility experiments on the sensor. It was found that the second measurement was considerably lower than the first measurement but the second and following measurements were substantially the same, indicating comparatively superior reproducibility.

Figure 37A:
FIG. 37(a) shows a sensor output in a potential measuring system.
Figure 37B:
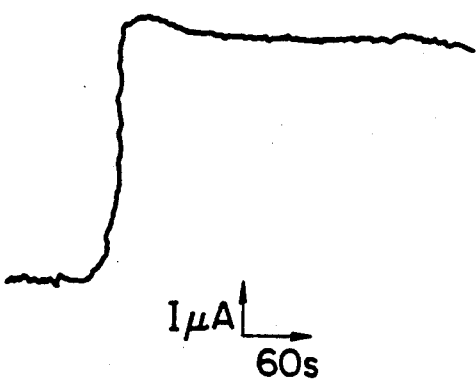
FIG. 37(b) is a waveform chart showing the sensor output in the current measuring system.

As shown, this embodiment of glucose sensor permits measurement of the glucose concentration up to a comparatively low concentration of about 10 mg/dl by adding electron movement medium to LB film 203 as enzyme-fixed film, and hence high sensitivity could be obtained. The most important reason for this is thought that compared to a signal-to-noise ratio of about 2 with a potential measurement process with the current process it is greatly improved to about 30 to obtain separation of signal and noise. FIG. 37(a) shows an example of the sensor output in the potential measurement system, and FIG. 37(b) shows an example of the sensor output of the current measurement system.

While in the above embodiment the glucose concentration was measured with the glucose sensor used as an enzyme sensor according to the invention, this is by no means limitative, and the invention is applicable as well to sensors for measuring the concentration of other substrates by using other enzymes.

What is claimed is:

1. An apparatus constructed and arranged for manufacturing a thin film by depositing sputtered particles on a predetermined surface of a substrate comprising:
   a vacuum chamber;
   a first front chamber formed adjacent to said vacuum chamber;
   a first on-off means for on-off operating the passage between said front chamber and vacuum chamber;
   a target base disposed in said vacuum chamber and for holding a target having at least a hydrophobic organic substance;
   a first moving mechanism for moving said target base between said vacuum chamber and first front chamber;
   a neutral beam generation means for irradiating said target supported by said target base with a neutral beam including ions with more than 95% thereof neutralized;
   a substrate base for supporting said substrate; and
   shutter means disposed between said substrate base and target base for controlling the passage and blocking of said sputtered particles.

2. The apparatus according to claim 1, which comprises a plurality of sputtering means each including said neutral beam generation means, target base and shutter means such that sputtered particles generated by each said sputtering means are collected on said substrate base.

3. The apparatus according to claim 1, which comprises a plurality of neutral beam generating means, said target being irradiated as common target by neutral beams shot from said individual neutral beam generation means to provide for improvement of the uniformity of film thickness distribution.

4. The apparatus according to claim 1, which further comprises a substrate base drive mechanism for rotating, linearly moving, angularly moving, and/or scanning said substrate base, thereby providing for uniform film thickness in a predetermined surface of said substrate.

5. The apparatus according to claim 4, wherein said substrate base is provided with a substrate temperature control means.

6. The apparatus according to claim 1, which further comprises a target base drive mechanism for rotating, linearly moving, angularly moving, and/or scanning said target base, thereby providing for uniform film thickness in a predetermined surface of said substrate.

7. The apparatus according to claim 1, which further comprises a second front chamber formed adjacent to said vacuum chamber, second on-off means for on-off operating the passage between said second front chamber and vacuum chamber, and second moving mechanism for moving said substrate base between said vacuum chamber and second front chamber.

8. The apparatus according to claim 1, which further comprises on-off means for on-off controlling the communication between said neutral beam generation means and vacuum chamber.

* * * * *

UNITED STATES PATENT AND TRADEMARK OFFICE
CERTIFICATE OF CORRECTION

PATENT NO. : 5,296,122
DATED : March 22, 1994
INVENTOR(S) : Teruaki KATSUBE et al It is certified that error appears in the above-indentified patent and that said Letters Patent is hereby corrected as shown below:

In Column 2, line 49, delete "B-D-glucose" and insert -- $\beta$-D-glucose --.

In Column 2, line 54, delete "gluconolactons" and insert -- gluconolactone --.

In Column 3, line 23, delete "stager" and insert -- stages --.

In Column 3, line 46, delete "gas." and insert -- gas, --.

In Column 4, line 20, delete "b 100" and insert -- 100 --.

In Column 9, line 12, delete "ah" and insert -- an --.

In Column 9, line 44, delete "2FCA → 2FCA$^{++2}$e" and insert
-- 2FCA → 2FCA$^+$ + 2e --.

In Column 12, line 53, delete "-(-CF$_3$ or CF$_2$-CF$_{22}$-)-" and insert
-- CF$_3$ or -(-CF$_2$-CF$_2$-)- --.

In Column 12, line 61, delete "-(-CF$_2$]CF$_{22}$-)-" and insert -- -(-CF$_2$-CF$_2$-)- --.

In Column 12, line 62, delete "including(CF$_2$-)$_n$-" and insert
-- including -(-CF-)$_n$- --.

In Column 12, line 63, delete "though" and insert -- thought --.

In Column 13, line 8, delete "bearing" and insert -- beam --.

In Column 13, line 67, after "beam" and before "11", insert -- gun --.

UNITED STATES PATENT AND TRADEMARK OFFICE
CERTIFICATE OF CORRECTION

PATENT NO. : 5,296,122

DATED : March 22, 1994

INVENTOR(S) : Teruaki KATSUBE et al

It is certified that error appears in the above-indentified patent and that said Letters Patent is hereby corrected as shown below:

In Column 14, line 41, delete "2 x $10^4$" and insert -- 2 x $10^{-6}$ --.
Col. 15, line 47, delete "can" (1st occurrence) and insert --gun--.
In Column 17, line 35, delete "key" and insert -- keV --.
In Column 17, line 37, delete "(UIAVC, IXK-7000)" and insert
    -- (ULAVC, IXK-7000) --.
In Column 17, line 40, delete "(si$_3$N$_4$)" and insert -- (Si$_3$N$_4$) --.
In Column 20, line 67, delete "5.0 gA" and insert -- 5.0 $\mu$A --.
In Column 22, line 30, delete "generating" and insert -- generation --.
In Column 22, line 37, delete "angularly" and insert -- arcularly --.
In Column 22, line 46, delete "angularly" and insert -- arcularly --.

Signed and Sealed this

Eighteenth Day of October, 1994

Attest:

BRUCE LEHMAN

*Attesting Officer*     *Commissioner of Patents and Trademarks*